United States Patent
Wang et al.

(10) Patent No.: US 8,518,667 B2
(45) Date of Patent: *Aug. 27, 2013

(54) KEX2 CLEAVAGE REGIONS OF RECOMBINANT FUSION PROTEINS

(75) Inventors: Huaming Wang, Fremont, CA (US); Michael Ward, San Francisco, CA (US)

(73) Assignee: Danisco US Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/472,296

(22) Filed: May 15, 2012

(65) Prior Publication Data

US 2013/0011877 A1 Jan. 10, 2013

Related U.S. Application Data

(63) Continuation of application No. 12/373,121, filed as application No. PCT/US2007/014476 on Jun. 21, 2007, now Pat. No. 8,198,046, which is a continuation-in-part of application No. 11/484,814, filed on Jul. 11, 2006, now abandoned.

(51) Int. Cl.
*C12P 21/06* (2006.01)
*C12N 15/00* (2006.01)
*C12N 1/20* (2006.01)
*C07H 21/02* (2006.01)

(52) U.S. Cl.
USPC ..................................................... 435/69.1

(58) Field of Classification Search
USPC .............. 435/69.1, 6, 252.3, 320.1; 536/23.1
See application file for complete search history.

(56) References Cited

U.S. PATENT DOCUMENTS

| | | | |
|---|---|---|---|
| 4,797,361 | A | 1/1989 | Montenecourt |
| 4,816,567 | A | 3/1989 | Cabilly et al. |
| 6,022,725 | A | 2/2000 | Fowler et al. |
| 6,103,490 | A | 8/2000 | Berka et al. |
| 6,265,204 | B1 | 7/2001 | Ward et al. |
| 6,268,328 | B1 | 7/2001 | Mitchinson et al. |
| 6,331,415 | B1 | 12/2001 | Cabilly et al. |
| 6,509,171 | B1 | 1/2003 | Berka et al. |
| 6,590,078 | B2 | 7/2003 | Ward et al. |
| 7,262,041 | B2 | 8/2007 | Baldwin et al. |
| 7,279,564 | B2 | 10/2007 | DeNobel et al. |
| 7,795,002 | B2 | 9/2010 | Davidson et al. |
| 2004/0018573 | A1 | 1/2004 | Power et al. |
| 2005/0153399 | A1 | 7/2005 | DeNobel et al. |
| 2005/0158825 | A1 | 7/2005 | Power et al. |
| 2005/0208623 | A1 | 9/2005 | Baldwin et al. |
| 2006/0003408 | A1 | 1/2006 | Dunn-Coleman et al. |
| 2006/0040353 | A1 | 2/2006 | Davidson et al. |
| 2006/0041113 | A1 | 2/2006 | Stafford et al. |

FOREIGN PATENT DOCUMENTS

| | | |
|---|---|---|
| EP | 0137280 | 8/1984 |
| EP | 0215594 | 3/1987 |
| EP | 244234 | 11/1987 |
| WO | WO 90/10075 | 9/1990 |
| WO | WO 96/00787 | 1/1996 |
| WO | WO 00/20555 | 4/2000 |
| WO | WO 01/18218 | 3/2001 |
| WO | WO 03/066818 | 8/2003 |
| WO | WO 03/089614 | 10/2003 |
| WO | WO 2005/001036 | 1/2005 |
| WO | WO 2005/093073 | 10/2005 |

OTHER PUBLICATIONS

Barclay et al., Efficient Transformation of Dictyostelium Discoideum Amoebae (1983) Molecular and Cellular Biology 3:2117-2130.

Bergquist et al., Production of Recombinant Bleaching Enyzmes from Thermophilic Microorganisms in Fungal Hosts. Biochem. Biotechnol. 100:165-176 (2002).

Berka et al., Molecular cloning and deletion of the gene encoding *aspergillopepsin A* from *Aspergillus awamori* (1990) Gene 86: 153-162.

Boel E. et al., Two Different Types of Intervening Sequences In The Glucoamylase Gene From *Aspergillus niger* (1984) EMBO J. 3: 1581-1585.

Boel et al., Glucoamylases G1 and G2 from *Aspergillus niger* are synthesized from two different but closely related mRNAs (1984) EMBO J. 3:1097-1102.

Brenner and Fuller, Structural and enzymatic characterization of a purified prohormone-processing enzyme:Secreted, soluble Kex2 protease (1992) Proc. Natl. Acad. Sci. 89:922-926.

Broekhuijsen et al., "Secretion of heterologous proteins by *Aspergillus niger*: Production of active human interleukin-6 in a protease-deficient mutant by KEX2-like processing of a glucoamylase-hIL6 fusion protein" (1993) J. Biotechnol. 31:135-145.

Campbell et al., Improved transformation efficiency of *Aspergillus niger* using the homologous niaD gene for nitrate reductase, Curr. Genet. 16:53-56 (1989).

Cao et al., Penicillopepsin-JT2, a recombinant enzyme from *Penicilium janthinellum* and the contribution of a hydrogen bond in subsite S3 to k(cat) (2000) Protein Sci. 9:991-1001.

Carter et al., Humanization of anti-p185[HER2] antibody for human cancer therapy, Proc. Natl. Acad. Sci. (1992) 89: 4285-4289.

Contreras et al., Efficient Kex2-Like Processing Of A Glucoamylase-interleukin-6 Fusion Protein by *Aspergillus nidulans* and Secretion of Mature Interleukin-6, (1991) Biotechnology 9:378-381.

Durand et al., Expression of a catalytic domain of a *Neocallimastix frontalis* endoxylanase gene (*xyn3*) in *Kluyveromyces lactis* and *Penicillium roqueforti*, Appl. Microbiol. Biotechnol. (1999) 52:208-214.

Foreman et al., Transcriptional Regulation of Biomass-degrading Enzymes in the Filamentous Fungus *Trichoderma reesei*, J. Biol. Chern 278:31988-31997, (2003).

Fowler, T. et al., Regulation of the *glaA* gene of *Aspergillus niger*, (1990) Curr. Genet. 18:537-545.

(Continued)

Primary Examiner — Maryam Monshipouri
(74) Attorney, Agent, or Firm — Danisco US Inc.

(57) ABSTRACT

The invention relates to a fusion DNA construct comprising a KEX2 region comprising a KEX2 site and a KEX2 site presequence immediately 5' to the KEX2 site, a fusion polypeptide, vectors and cells comprising the fusion DNA construct, methods for producing desired proteins from filamentous fungal cells and methods for enhancing the secretion and/or cleavage of a desired protein from a cell.

23 Claims, 9 Drawing Sheets

(56) References Cited

OTHER PUBLICATIONS

Fuller et al., "Yeast Prohormone Processing Enzyme (*KEX2* gene product) is a $Ca^{2+}$-dependent serine protease" (1989) Proc. Natl. Acad. Sci. USA, 86:1434-1438.
Gines et al., *Aspergillus oryzae* has two nearly identical Taka-amylase genes, each containing eight introns (1989) Gene 79: 107-117.
Goller et al., Role of Endoproteolytic Dibasic Protein Processing in Maturation of Secretory Proteins In *Trichoderma reesei* (1998) Appl. Environ. Microbiol. 64:3202-3208.
Gouka et al., Efficient production of secreted proteins by *Aspergillus*: progress, limitations and prospects, (1997) Appl. Microbiol. Biotechnol. 47:1-11.
Gwynne et al., Genetically Engineered Secretion of Active Human Interferon and a Bacterial Endoglucanase From *Aspergillus nidulans*, (1987) Bio/Technology 5:713-719.
Harkki et al., Genetic Engineering of *Trichoderma* to Produce Strains with Novel Cellulase Profiles (1991); Enzyme Microb. Technol. 13:227-233.
Harkki et al., A Novel Fungal Expression System: Secretion of Active Calf Chymosin From The Filamentous Fungus *Trichoderma reesei*, (1989) Bio/Technol. 7:596-603.
Hartley, J.L. et al., DNA Cloning Using In Vitro Site-Specific Recombination (2000) Genome Research 10:1788-1795.
Hynes et al., Isolation of Genomic Clones Containing the amdS Gene of *Aspergillus nidulans* and Their Use in the Analysis of Structural and Regulatory Mutations (1983) Mol. Cell Biol. 3: 1430-1439.
Ilmen, M. et al., Regulation of Celluase Gene Expression in the Filamentous Fungus *Trichoderma Reesei* (1997) App. Environ. Microbiol. 63:1298-1306.
Innis et al., Expression, Glycosylation, and Secretion of an *Aspergillus* Glucoamylase by *Saccharomyces cerevisiae* (1985) Sci. 228:21-26.
Jalving et al., Characterization of the Kexin-Like Maturase of *Aspergillus niger* (2000) Appl. Environ. Microbiol. 66:363-368.
Jeenes et al., A Truncated glucoamylase gene fusion for heterologous protein secretion from *Aspergillus niger* (1993) FEMS Microbiol. Lett. 107:267-273.
Kelley et al., Transformation of *Aspergillus niger* by the *amdS* gene of *Aspergillus nidulans* (1985) EMBO J. 4:475-479.
Korman et al., Cloning, characterization, and expression of two a-amylase genes from *Aspergillus niger var. awamori* (1990) Curr. Genet 17:203-212.
La Grange et al., Expression of a *Trichoderma reesei* B-Xylanase Gene (XYN2) in *Saccharomyces cerevisiae* (1996) Appl. Environ. Microbiol. 62:1036-1044.
Libby et al., Effect of amino acid deletions in the O-glycosylated region of *Aspergillus awamori glucoamylase* (1994) Protein Engineering 7:1109-1114.
Lockington et al., Cloning and characterization of the ethanol utilization regulon in *Aspergillus nidulans* (1986) Gene 33: 137-149.
MacKenzie et al., (1998) Aberrant processing of wild-type and mutant bovine pancreatic trypsin inhibitor secreted by *Aspergillus niger*, J. Biotechnology 63:137-146.
McKnight et al., Nucleotide Sequence of the Triosephosphate Isomerase Gene From *Aspergillus nidulans* Implications for a Differential Loss of Introns (1986) Cell 46: 143-147.
Mikosch et al., "Secretion of active human mucus proteinase inhibitor by processing of a glucoamylase-inhibitor fusion protein." J. Biotechnol., (1996) 52, 97-106.
Mullaney et al., Primary structure of the trpC gene from *Aspergillus nidulans* (1985) Mol. Gen. Genet. 199:37-45.
Nunberg et al., Molecular Cloning and Characterization of the Glucoamylase Gene of *Aspegillus awamori*, (1984) Mol. Cell. Biol. 4: 2306-2353.
Paloheimo et al., High-Yield Production of a Bacterial Xylanase in the Filamentous Fungus *Trichoderma reesei* Requires A Carrier Polypeptide With An Intact Domain Structure Applied and Environmental Microbiology (2003) 69: 7073-7082.
Pennell and Eldin, In Vitro production of recombinant antibody fragments in *Pichia pastoris* (1998) Res. Immunol. 149:599-603.
Penttila et al., A versatile transformation system for the cellulolytic filamentous fungus *Trichoderma reesei* (1987) Gene 61: 155-164.
Pourquie, J. et al., "Scale Up of Cellulase Production and Utilization", Biochemistry and Genetics of Cellulose Degradation, eds. Aubert, J. P. et al., Academic Press, pp. 71-86, 1988.
Sheir-Neiss et al., Characterization of the secreted, (1984) Appl. Microbiol. Biotechnology 20:46-53. cellulose of *Trichoderma reesei* wild type and mutants during controlled fermentations.
Shoemaker et al., Molecular cloning of exo-cellobiohydrolase I Derived From *Trichoderma reesei* Strain 1.27, (1981) Bio/Technology 1: 691-696.
Spencer, Determinants of the fidelity of processing glucoamylase-lysozyme fusions by *Aspergillus niger* (1998) Eur. J. Biochem 258: 107-112.
Torronen, A. et al., "The two major xylanases from *Trichoderma reesei*: characterization of both enzymes and genes." Bio/Technology 10(11): 1461-5, Nov. 1992.
Tsuchiya et al., High Level Secretion of Calf Chymosin (1994) Biosci. Biotech. Biochem. 58: 895-899.Using A Gluocoamylase-prochymosin Fusion Gene in *Aspergillus* oryzae.
Van Hartingsveldt, W. et al., Development of a homologous transformation system for *Aspergillus niger* based on the *pyrG* gene (1987) Mol. Gen. Genet. 206:71-75.
Verma et al., Antibody engineering: Comparison of bacterial, yeast, insect and mammalian expression systems. Antibody engineering: Comparison of bacterial, yeast, insect and mammalian expression systems (1998) J. Immunological Methods 216:165-181.
Ward et al., Improved Production of Chymosin In *Aspergillus* by expression as a glucoamylase-chymosin fusion (1990) Bio/Technology 8:435-440.
Ward, M. et al., Use of *Aspergillus* overproducing mutants cured for integrated plasmid, to overproduce heterologous proteins (1993) Appl. Microbiol. Biotech. 39:738-743.
Ward et al., A System for Production of Commercial Quantities of Human Lactoferrin: A Broad Spectrum Natural Antibotic (1995) Bio/Technology 13:498-503.
Ward et al., Characterization of Humanized Antibodies Secreted by *Aspergillus niger* (2004) Appl. Environ. Microbiol. 70:2567-2576.
Yelton et al., Transformation of *Aspergillus nidulans* by using a trpC plasmid (1984) Proc. Natl. Acad. Sci. 81:1470-1474.

DNA Sequence of pTrex4-her2 Light Chain DNA2.0 (10885 Bases)
(SEQ ID NO: 103)

```
AAGCTTAATACTTCTCGAGCTCTGTACATGTCCGGTCGCGACGTACGCGTATCGATG
GCGCCAGCTGCAGGCGGCCGCCTGCAGCCACTTGCAGTCCCGTGGAATTCTCACGGT
GAATGTAGGCCTTTTGTAGGGTAGGAATTGTCACTCAAGCACCCCCAACCTCCATTA
CGCCTCCCCCATAGAGTTCCCAATCAGTGAGTCATGGCACTGTTCTCAAATAGATTG
GGGAGAAGTTGACTTCCGCCCAGAGCTGAAGGTCGCACAACCGCATGATATAGGGTC
GGCAACGGCAAAAAGCACGTGGCTCACCGAAAAGCAAGATGTTTGCGATCTAACAT
CCAGGAACCTGGATACATCCATCATCACGCACGACCACTTTGATCTGCTGGTAAACT
CGTATTCGCCCTAAACCGAAGTGACGTGGTAAATCTACACGTGGGCCCCTTTCGGTA
TACTGCGTGTGTCTTCTAGGTGCCATTCTTTTCCCTTCCTCTAGTGTTGAATTGT
TTGTGTTGGAGTCCGAGCTGTAACTACCTCTGAATCTCTGGAGAATGGTGGACTAAC
GACTACCGTGCACCTGCATCATGTATATAATAGTGATCCTGAGAAGGGGGTTTGGA
GCAATGTGGGACTTTGATGGTCATCAAACAAAGAACGAAGACGCCTCTTTTGCAAAG
TTTTGTTTCGGCTACGGTGAAGAACTGGATACTTGTTGTGTCTTCTGTGTATTTTTG
TGGCAACAAGAGGCCAGAGACAATCTATTCAAACACCAAGCTTGCTCTTTTGAGCTA
CAAGAACCTGTGGGGTATATATCTAGAGTTGTGAAGTCGGTAATCCCGCTGTATAGT
AATACGAGTCGCATCTAAATACTCCGAAGCTGCTGCGAACCCGGAGAATCGAGATGT
GCTGGAAAGCTTCTAGCGAGCGGCTAAATTAGCATGAAAGGCTATGAGAAATTCTGG
AGACGGCTTGTTGAATCATGGCGTTCCATTCTTCGACAAGCAAAGCGTTCCGTCGCA
GTAGCAGGCACTCATTCCCGAAAAAACTCGGAGATTCCTAAGTAGCGATGGAACCGG
AATAATATAATAGGCAATACATTGAGTTGCCTCGACGGTTGCAATGCAGGGTACTG
AGCTTGGACATAACTGTTCCGTACCCCACCTCTTCTCAACCTTTGGCGTTTCCCTGA
TTCAGCGTACCCGTACAAGTCGTAATCACTATTAACCCAGACTGACCGGACGTGTTT
TGCCCTTCATTTGGAGAAATAATGTCATTGCGATGTGTAATTTGCCTGCTTGACCGA
CTGGGGCTGTTCGAAGCCCGAATGTAGGATTGTTATCCGAACTCTGCTCGTAGAGGC
ATGTTGTGAATCTGTGTCGGGCAGGACACGCCTCGAAGGTTCACGGCAAGGGAAACC
ACCGATAGCAGTGTCTAGTAGCAACCTGTAAAGCCGCAATGCAGCATCACTGGAAAA
TACAAACCAATGGCTAAAAGTACATAAGTTAATGCCTAAAGAAGTCATATACCAGCG
GCTAATAATTGTACAATCAAGTGGCTAAACGTACCGTAATTTGCCAACGGCTTGTGG
GGTTGCAGAAGCAACGGCAAAGCCCCACTTCCCCACGTTTGTTTCTTCACTCAGTCC
AATCTCAGCTGGTGATCCCCCAATTGGGTCGCTTGTTTGTTCCGGTGAAGTGAAAGA
AGACAGAGGTAAGAATGTCTGACTCGGAGCGTTTTGCATACAACCAAGGGCAGTGAT
GGAAGACAGTGAAATGTTGACATTCAAGGAGTATTTAGCCAGGGATGCTTGAGTGTA
TCGTGTAAGGAGGTTTGTCTGCCGATACGACGAATACTGTATAGTCACTTCTGATGA
AGTGGTCCATATTGAAATGTAAGTCGGCACTGAACAGGCAAAAGATTGAGTTGAAAC
TGCCTAAGATCTCGGGCCCTCGGGCCTTCGGCCTTTGGGTGTACATGTTTGTGCTCC
GGGCAAATGCAAAGTGTGGTAGGATCGAACACACTGCTGCCTTTACCAAGCAGCTGA
GGGTATGTGATAGGCAAATGTTCAGGGCCACTGCATGGTTTCGAATAGAAAGAGAA
GCTTAGCCAAGAACAATAGCCGATAAAGATAGCCTCATTAAACGGAATGAGCTAGTA
GGCAAAGTCAGCGAATGTGTATATATAAAGGTTCGAGGTCCGTGCCTCCCTCATGCT
CTCCCCATCTACTCATCAACTCAGATCCTCCAGGAGACTTGTACACCATCTTTTGAG
GCACAGAAACCCAATAGTCAACCGCGGACTGCGCATCATGTATCGGAAGTTGGCCGT
CATCTCGGCCTTCTTGGCCACAGCTCGTGCTCAGTCGGCCTGCACTCTCCAATCGGA
GACTCACCCGCCTCTGACATGGCAG
```

FIG. 3A

```
AAATGCTCGTCTGGTGGCACTTGCACTCAACAGACAGGCTCCGTGGTCATCGACGCC
AACTGGCGCTGGACTCACGCTACGAACAGCAGCACGAACTGCTACGATGGCAACACT
TGGAGCTCGACCCTATGTCCTGACAACGAGACCTGCGCGAAGAACTGCTGTCTGGAC
GGTGCCGCCTACGCGTCCACGTACGGAGTTACCACGAGCGGTAACAGCCTCTCCATT
GGCTTTGTCACCCAGTCTGCGCAGAAGAACGTTGGCGCTCGCCTTTACCTTATGGCG
AGCGACACGACCTACCAGGAATTCACCCTGCTTGGCAACGAGTTCTCTTTCGATGTT
GATGTTTCGCAGCTGCCGTAAGTGACTTACCATGAACCCCTGACGTATCTTCTTGTG
GGCTCCCAGCTGACTGGCCAATTTAAGGTGCGGCTTGAACGGAGCTCTCTACTTCGT
GTCCATGGACGCGGATGGTGGCGTGAGCAAGTATCCCACCAACACCGCTGGCGCCAA
GTACGGCACGGGGTACTGTGACAGCCAGTGTCCCCGCGATCTGAAGTTCATCAATGG
CCAGGCCAACGTTGAGGGCTGGGAGCCGTCATCCAACAACGCAAACACGGGCATTGG
AGGACACGGAAGCTGCTGCTCTGAGATGGATATCTGGGAGGCCAACTCCATCTCCGA
GGCTCTTACCCCCACCCTTGCACGACTGTCGGCCAGGAGATCTGCGAGGGTGATGG
GTGCGGCGGAACTTACTCCGATAACAGATATGGCGGCACTTGCGATCCCGATGGCTG
CGACTGGAACCCATACCGCCTGGGCAACACCAGCTTCTACGGCCCTGGCTCAAGCTT
TACCCTCGATACCACCAAGAAATTGACCGTTGTCACCCAGTTCGAGACGTCGGGTGC
CATCAACCGATACTATGTCCAGAATGGCGTCACTTTCCAGCAGCCCAACGCCGAGCT
TGGTAGTTACTCTGGCAACGAGCTCAACGATGATTACTGCACAGCTGAGGAGGCAGA
ATTCGGCGGATCCTCTTTCTCAGACAAGGGCGGCCTGACTCAGTTCAAGAAGGCTAC
CTCTGGCGGCATGGTTCTGGTCATGAGTCTGTGGGATGATGTGAGTTTGATGGACAA
ACATGCGCGTTGACAAAGAGTCAAGCAGCTGACTGAGATGTTACAGTACTACGCCAA
CATGCTGTGGCTGGACTCCACCTACCCGACAAACGAGACCTCCTCCACACCCGGTGC
CGTGCGCGGAAGCTGCTCCACCAGCTCCGGTGTCCCTGCTCAGGTCAATCTCAGTC
TCCCAACGCCAAGGTCACCTTCTCCAACATCAAGTTCGGACCCATTGGCAGCACCGG
CAACCCTAGCGGCGGCAACCCTCCCGGCGGAAACCCGCCTGGCACCACCACCACCCG
CCGCCCAGCCACTACCACTGGAAGCTCTCCCGGACCTACTAGTAAACGCGGTGGCGG
TGATATTCAAATGACACAATCTCCTTCTTCTCTGTCAGCCTCAGTGGGCGACCGTGT
GACGATTACTTGCCGCGCCTCTCAGGACGTTAACACTGCCGTCGCATGGTACCAGCA
GAAGCCAGGCAAGGCGCCCAAGCTTCTGATTTACAGCGCTTCGTTCCTGTACTCTGG
CGTGCCATCCCGCTTCTCTGGCAGCCAAGCGGCACGGATTTCACCCTGACCATTTC
GTCCCTGCAGCCCGAGGATTTCGCCACGTATTACTGCCAGCAGCACTACACCACTCC
ACCCACCTTTGGCCAAGGAACGAGAGTCGAAATCACTCGCACGGTCGCTGCCCCTTC
AGTCTTCATCTTCCCCCCAGCGACGAACAGCTGAAGTCTGGTACGGCCAGCGTCGT
TTGCTTGCTTAATAACTTCTATCCGCGAGAGGCGAAGGTCCAATGGAAGGTTGATAA
CGTTCTGCAGTCCGGCAATTCGCAGGAGAGCGTGACCGAGCAGGATTCAAAGGATAG
CACCTACTCACTCAGCAGCACCCTGACGTTGTCCAAGGCCGATTACGAGAAGCATAA
GTTGTATGCATGCGAGGTCACCCACCAGGGACTGTCAAGCCCAGTTACCAAGTCGTT
CAATCGAGGCGAGTGCTAAGGCGCGCCGCGCGCCAGCTCCGTGCGAAAGCCTGACGC
ACCGGTAGATTCTTGGTGAGCCCGTATCATGACGGCGGCGGGAGCTACATGGCCCCG
GGTGATTTATTTTTTTTGTATCTACTTCTGACCCTTTTCAAATATACGGTCAACTCA
TCTTTCACTGGAGATGCGGCCTGCTTGGTATTGCGATGTTGTCAGCTTGGCAAATTG
TGGCTTTCGAAAACACAAAACGATTCCTTAGTAGCCATGCATTTTAAGATAACGGAA
TAGAAGAAGAGGAAATTAAAAAAAAAAAAAAACAAACATCCCGTTCATAACCCGT
AGAATCGCCGCTCTTCGTGTATCCCAGTACCAGTTTATTTTGAATAGCTCGCCCGCT
GGAGAGCATCCTGAATGCAAGTAACAACC
```

*FIG. 3B*

```
GTAGAGGCTGACACGGCAGGTGTTGCTAGGGAGCGTCGTGTTCTACAAGGCCAGACG
TCTTCGCGGTTGATATATATGTATGTTTGACTGCAGGCTGCTCAGCGACGACAGTCA
AGTTCGCCCTCGCTGCTTGTGCAATAATCGCAGTGGGGAAGCCACACCGTGACTCCC
ATCTTTCAGTAAAGCTCTGTTGGTGTTTATCAGCAATACACGTAATTTAAACTCGTT
AGCATGGGGCTGATAGCTTAATTACCGTTTACCAGTGCCGCGGTTCTGCAGCTTTCC
TTGGCCCGTAAAATTCGGCGAAGCCAGCCAATCACCAGCTAGGCACCAGCTAAACCC
TATAATTAGTCTCTTATCAACACCATCCGCTCCCCGGGATCAATGAGGAGAATGAG
GGGGATGCGGGCTAAAGAAGCCTACATAACCCTCATGCCAACTCCCAGTTTACACT
CGTCGAGCCAACATCCTGACTATAAGCTAACACAGAATGCCTCAATCCTGGGAAGAA
CTGGCCGCTGATAAGCGCGCCCGCCTCGCAAAAACCATCCCTGATGAATGGAAAGTC
CAGACGCTGCCTGCGGAAGACAGCGTTATTGATTTCCCAAAGAAATCGGGGATCCTT
TCAGAGGCCGAACTGAAGATCACAGAGGCCTCCGCTGCAGATCTTGTGTCCAAGCTG
GCGGCCGGAGAGTTGACCTCGGTGGAAGTTACGCTAGCATTCTGTAAACGGGCAGCA
ATCGCCCAGCAGTTAGTAGGGTCCCCTCTACCTCTCAGGGAGATGTAACAACGCCAC
CTTATGGGACTATCAAGCTGACGCTGGCTTCTGTGCAGACAAACTGCGCCCACGAGT
TCTTCCCTGACGCCGCTCTCGCGCAGGCAAGGGAACTCGATGAATACTACGCAAAGC
ACAAGAGACCCGTTGGTCCACTCCATGGCCTCCCCATCTCTCTCAAAGACCAGCTTC
GAGTCAAGGTACACCGTTGCCCCTAAGTCGTTAGATGTCCCTTTTTGTCAGCTAACA
TATGCCACCAGGGCTACGAAACATCAATGGGCTACATCTCATGGCTAAACAAGTACG
ACGAAGGGGACTCGGTTCTGACAACCATGCTCCGCAAAGCCGGTGCCGTCTTCTACG
TCAAGACCTCTGTCCCGCAGACCCTGATGGTCTGCGAGACAGTCAACAACATCATCG
GGCGCACCGTCAACCCACGCAACAAGAACTGGTCGTGCGGCGGCAGTTCTGGTGGTG
AGGGTGCGATCGTTGGGATTCGTGGTGGCGTCATCGGTGTAGGAACGGATATCGGTG
GCTCGATTCGAGTGCCGGCCGCGTTCAACTTCCTGTACGGTCTAAGGCCGAGTCATG
GGCGGCTGCCGTATGCAAAGATGGCGAACAGCATGGAGGGTCAGGAGACGGTGCACA
GCGTTGTCGGGCCGATTACGCACTCTGTTGAGGGTGAGTCCTTCGCCTCTTCCTTCT
TTTCCTGCTCTATACCAGGCCTCCACTGTCCTCCTTTCTTGCTTTTTATACTATATA
CGAGACCGGCAGTCACTGATGAAGTATGTTAGACCTCCGCCTCTTCACCAAATCCGT
CCTCGGTCAGGAGCCATGGAAATACGACTCCAAGGTCATCCCCATGCCCTGGCGCCA
GTCCGAGTCGGACATTATTGCCTCCAAGATCAAGAACGGCGGGCTCAATATCGGCTA
CTACAACTTCGACGGCAATGTCCTTCCACACCCTCCTATCCTGCGCGGCGTGGAAAC
CACCGTCGCCGCACTCGCCAAAGCCGGTCACACCGTGACCCCGTGGACGCCATACAA
GCACGATTTCGGCCACGATCTCATCTCCCATATCTACGCGGCTGACGGCAGCGCCGA
CGTAATGCGCGATATCAGTGCATCCGGCGAGCCGGCGATTCCAAATATCAAAGACCT
ACTGAACCCGAACATCAAAGCTGTTAACATGAACGAGCTCTGGGACACGCATCTCCA
GAAGTGGAATTACCAGATGGAGTACCTTGAGAAATGGCGGGAGGCTGAAGAAAAGGC
CGGGAAGGAACTGGACGCCATCATCGCGCCGATTACGCCTACCGCTGCGGTACGGCA
TGACCAGTTCCGGTACTATGGGTATGCCTCTGTGATCAACCTGCTGGATTTCACGAG
CGTGGTTGTTCCGGTTACCTTTGCGGATAAGAACATCGATAAGAAGAATGAGAGTTT
CAAGGCGGTTAGTGAGCTTGATGCCCTCGTGCAGGAAGAGTATGATCCGGAGGCGTA
CCATGGGGCACCGGTTGCAGTGCAGGTTATCGGACGGAGACTCAGTGAAGAGAGGAC
GTTGGCGATTGCAGAGGAAGTGGGGAAGTTGCTGGGAAATGTGGTGACTCCATAGCT
AATAAGTGTCAGATAGCAATTTGCACAAGAAATCAATACCAGCAACTGTAAATAAGC
GCTGAAGTGACCATGCCATGCTACGAAAGAGCAGAAAAAACCTGCCGTAGAACCGA
AGAGATATGACACGCTTCCATCTCTCAAA
```

*FIG. 3C*

```
GGAAGAATCCCTTCAGGGTTGCGTTTCCAGTCTAGACACGTATAACGGCACAAGTGT
CTCTCACCAAATGGGTTATATCTCAAATGTGATCTAAGGATGGAAAGCCCAGAATCT
AGGCCTATTAATATTCCGGAGTATACGTAGCCGGCTAACGTTAACAACCGGTACCTC
TAGAACTATAGCTAGCATGCGCAAATTTAAAGCGCTGATATCGATCGCGCGCAGATC
CATATATAGGGCCCGGGTTATAATTACCTCAGGTCGACGTCCCATGGCCATTCGAAT
TCGTAATCATGGTCATAGCTGTTTCCTGTGTGAAATTGTTATCCGCTCACAATTCCA
CACAACATACGAGCCGGAAGCATAAAGTGTAAAGCCTGGGGTGCCTAATGAGTGAGC
TAACTCACATTAATTGCGTTGCGCTCACTGCCCGCTTTCCAGTCGGGAAACCTGTCG
TGCCAGCTGCATTAATGAATCGGCCAACGCGCGGGAGAGGCGGTTTGCGTATTGGG
CGCTCTTCCGCTTCCTCGCTCACTGACTCGCTGCGCTCGGTCGTTCGGCTGCGGCGA
GCGGTATCAGCTCACTCAAAGGCGGTAATACGGTTATCCACAGAATCAGGGGATAAC
GCAGGAAAGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAAAAATCGA
CGCTCAAGTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACCCCCCGTT
CAGCCCGACCGCTGCGCCTTATCCGGTAACTATCGTCTTGAGTCCAACCCGGTAAGA
CACGACTTATCGCCACTGGCAGCAGCCACTGGTAACAGGATTAGCAGAGCGAGGTAT
GTAGGCGGTGCTACAGAGTTCTTGAAGTGGTGGCCTAACTACGGCTACACTAGAAGA
ACAGTATTTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGTTTGCAAG
CAGCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGATTA
TCAAAAAGGATCTTCACCTAGATCCTTTTAAATTAAAAATGAAGTTTTAAATCAATC
TAAAGTATATATGAGTAAACTTGGTCTGACAGTTACCAATGCTTAATCAGTGAGGCA
CCTATCTCAGCGATCTGTCTATTTCGTTCATCCATAGTTGCCTGACTCCCCGTCGTG
TAGATAACTACGATACGGGAGGGCTTACCATCTGGCCCCAGTGCTGCAATGATACCG
CGAGACCCACGCTCACCGGCTCCAGATTTATCAGCAATAAACCAGCCAGCCGGAAGG
GCCGAGCGCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGTTGTTGCC
ATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTTATCACTC
ATGGTTATGGCAGCACTGCATAATTCTCTTACTGTCATGCCATCCGTAAGATGCTTT
TCTGTGACTGGTGAGTACTCAACCAAGTCATTCTGAGAATAGTGTATGCGGCGACCG
AGTTGCTCTTGCCCGGCGTCAATACGGGATAATACCGCGCCACATAGCAGAACTTTA
AAAGTGCTCATCATTGGAAAACGTTCTTCGGGGCGAAAACTCTCAAGGATCTTACCG
CTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAA
AAGGGAATAAGGGCGACACGGAAATGTTGAATACTCATACTCTTCCTTTTTCAATAT
TATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCACCTGAC
GTCTAAGAAACCATTATTATCATGACATTAACCTATAAAAATAGGCGTATCACGAGG
CCCTTTCGTCTCGCGCGTTTCGGTGATGA
```

FIG. 3D

```
CGGTGAAAACCTCTGACACATGCAGCTCCCGGAGACGGTCACAGCTTGTCTGTAAGC
GGATGCCGGGAGCAGACAAGCCCGTCAGGGCGCGTCAGCGGGTGTTGGCGGGTGTCG
GGGCTGGCTTAACTATGCGGCATCAGAGCAGATTGTACTGAGAGTGCACCATAAAAT
TGTAAACGTTAATATTTTGTTAAAATTCGCGTTAAATTTTTGTTAAATCAGCTCATT
TTTTAACCAATAGGCCGAAATCGGCAAAATCCCTTATAAATCAAAAGAATAGCCCGA
GATAGGGTTGAGTGTTGTTCCAGTTTGGAACAAGAGTCCACTATTAAAGAACGTGGA
CTCCAACGTCAAAGGGCGAAAAACCGTCTATCAGGGCGATGGCCCACTACGTGAACC
ATCACCCAAATCAAGTTTTTTGGGGTCGAGGTGCCGTAAAGCACTAAATCGGAACCC
TAAAGGGAGCCCCCGATTTAGAGCTTGACGGGGAAAGCCGGCGAACGTGGCGAGAAA
GGAAGGGAAGAAAGCGAAAGGAGCGGGCGCTAGGGCGCTGGCAAGTGTAGCGGTCAC
GCTGCGCGTAACCACCACACCCGCCGCGCTTAATGCGCCGCTACAGGGCGCGTACTA
TGGTTGCTTTGACGTATGCGGTGTGAAATACCGCACAGATGCGTAAGGAGAAAATAC
CGCATCAGGCGCCATTCGCCATTCAGGCTGCGCAACTGTTGGGAAGGGCGATCGGTG
CGGGCCTCTTCGCTATTACGCCAGCTGGCGAAAGGGGGATGTGCTGCAAGGCGATTA
AGTTGGGTAACGCCAGGGTTTTCCCAGTCACGACGTTGTAAAACGACGGCCAGTGCC
```

KEX2 CLEAVAGE REGIONS OF RECOMBINANT FUSION PROTEINS

CROSS-REFERENCE TO RELATED APPLICATIONS

This application is a continuation of U.S. application Ser. No. 12/373,121, filed Aug. 31, 2009, now issued as U.S. Pat. No. 8,198,046, issued on Jun. 12, 2012, which is a National Stage entry of PCT/US07/14476, filed Jun. 21, 2007, and is a continuation-in-part of U.S. Ser. No. 11/484,814, filed Jul. 11, 2006 now abandoned, which is hereby incorporated by reference.

STATEMENT AS TO RIGHTS TO INVENTIONS MADE UNDER FEDERALLY SPONSORED RESEARCH AND DEVELOPMENT

Portions of this work were funded by Contract No. W911NF-05-C-0072 by the Defense Advanced Research Projects Agency (DARPA) of the U.S. Accordingly, the United States Government may have certain rights in this invention.

SEQUENCE LISTING

The sequence listing submitted via EFS, in compliance with 37 C.F.R. §1.52(e), is incorporated herein by reference. The sequence listing text file submitted via EFS contains the file "GC908US_CorrectedSequenceListing.text", created on Aug. 30, 2012, which is 42,267 bytes in size.

FIELD OF THE INVENTION

The present invention relates to increased secretion and cleavage of desired proteins, such as functional antibody proteins and industrial enzymes from filamentous fungi. The invention discloses fusion DNA constructs, vectors and fusion polypeptides incorporating KEX2 regions for protein cleavage and methods of producing desired proteins.

BACKGROUND

During protein secretion in a fungal cell, certain proteins are cleaved by KEX2, a member of the KEX2 or "kexin" family of serine peptidase (EC 3.4.21.61). KEX2 is a highly specific calcium-dependent endopeptidase that cleaves the peptide bond that is immediately C-terminal to a pair of basic amino acids (i.e., the "KEX2 site") in a protein substrate during secretion of that protein. KEX2 proteins generally contain a cysteine residue near the histidine residue of its active site and are inhibited by p-mercuribenzoate. The founding member of this group, the KEX2 peptidase of *S. cerevisiae* (Fuller et al., 1989, Proc. Natl. Acad. Sci. USA 86:1434-1438), cleaves the α-factor pheromone and killer toxin precursors during their secretion.

Production of fusion polypeptides has been reported in a number of organisms including *E. coli*, yeast and filamentous fungi. For example, bovine chymosin has been produced in *Aspergillus niger* as a fusion to full length glucoamylase (GAI) (Ward et al., (1990) Bio/technology 8:435-440; U.S. Pat. No. 6,265,204 and U.S. Pat. No. 6,590,078); human interleukin 6 (hIL6) has been produced in *Aspergillus nidulans* as a fusion to full-length *A. niger* glucoamylase (GAI) (Contreras et al., (1991) Biotechnology 9:378-381); hen egg white lysozyme (Jeenes et al., (1993) FEMS Microbiol. Lett. 107:267-273) and human lactoferrin (Ward et al., (1995) Bio/Technology 13:498-503) have been produced in *Aspergillus niger* as a fusion to residues 1-498 of glucoamylase; and bovine chymosin has been produced in *Aspergillus niger* as a fusion with full length native alpha amylase (Korman et al., (1990) Curr. Genet. 17: 203-212) and in *Aspergillus oryzae* as a fusion with truncated forms of *A. oryzae* glucoamylase (Tsuchiya et al., (1994) Biosci. Biotech. Biochem. 58: 895-899). Reference is also made to Shoemaker et al., 1981 Bio/Technology 1: 691-696; Nunberg et al., (1984) Mol. Cell. Biol. 4:2306-2315 and Boel et al., (1984) EMBO J. 3:1097-1102. In some of these fusion proteins, a KEX2 protease recognition site (Lys-Arg) has been inserted between a glucoamylase and a desired protein (e.g., Contreras et al., 1991 and Ward et al., 1995). The inventors of the present invention have found that protein secretion and/or protein cleavage may be enhanced in a fusion protein when the KEX2 recognition site has been manipulated to include an amino acid KEX2 site pre-sequence.

Specific literature of interest includes: Ward et al., (2004) Appl. Environ. Microbiol. 70:2567-2576; Goller et al., (1998) Appl. Environ. Microbiol. 64:3202-3208; La Grange et al., (1996) Appl. Environ. Microbiol. 62:1036-1044; Bergquist et al., (2002) Biochem. Biotechnol. 100:165-176; Spencer et al., (1998) Eur. J. Biochem. 258:107-112; Jalving et al., (2000) Appl. Environ. Microbiol. 66:363-368); Brenner and Fuller (1992) Proc. Natl. Acad. Sci. 89:922-926; Durand et al., (1999) Appl. Microbiol. Biotechnol. 52: 208-214; Ahn et al., (2004) Appl. Microbiol. Biotechnol. 64:833-839; Gouka et al., (1997) Appl Microbiol Biotechnol. 47:1-11 Broekhuijsen et al., (1993) J. Biotechnol. 31:135-145; MacKenzie et al., (1998) J. Biotechnol. 63:137-146 and published patent applications 20040018573 and 20050158825. Also U.S. Pat. No. 4,816,567 and U.S. Pat. No. 6,331,415 disclose processes for producing immunoglobulin molecules in recombinant host cells. The above cited literature is incorporated by reference herein for all purposes.

While numerous methods are available for the production of industrial enzymes and therapeutic proteins, there remains a need for alternative methods of protein production and particularly for therapeutic protein production, such as antibody production, which will result in relatively quick scale up time and high levels of produced protein with limited risk of contamination by viral or other adventitious agents. The present invention answers this need.

SUMMARY OF THE INVENTION

A fusion DNA construct, vectors, a fusion polypeptide, a cell comprising the fusion DNA construct, and methods for enhancing the secretion and/or cleavage of a desired protein from a cell are provided. More specifically, a KEX2 region encompassed by the invention has been included in a fusion polypeptide to provide for cleavage of a desired protein from the fusion polypeptide. Accordingly, the invention pertains to a KEX2 region for protein cleavage.

In some embodiments, the invention relates to a fusion DNA construct encoding a fusion polypeptide, comprising in operable linkage from the 5' end of said construct, a promoter; a first DNA molecule encoding a signal sequence; a second DNA molecule encoding a carrier protein; a third DNA molecule encoding a KEX2 region, said KEX2 region comprising a KEX2 site and a KEX2 site pre-sequence immediately 5' to the KEX2 site; and a fourth DNA molecule encoding a desired protein. In some aspects of this embodiment, the invention relates to a vector, such as an expression vector, which comprises the fusion DNA construct, and in other aspects the invention relates to host cells transformed with the vector or comprising the fusion DNA construct.

In other embodiments, the invention relates to a fusion polypeptide comprising from an amino terminus of said fusion polypeptide a first amino acid sequence comprising a signal sequence functional as a secretory sequence; a second amino acid sequence comprising a carrier protein; a third amino acid sequence comprising a KEX2 region, said KEX2 region comprising a KEX2 site and a KEX2 site pre-sequence immediately N-terminal to said KEX2 site; and a fourth amino acid sequence comprising a desired protein.

In further embodiments, the invention relates to a KEX2 region ($X_4X_3X_2X_1B_1B_2$) comprising a KEX2 site ($B_1B_2$) and a KEX2 site pre-sequence ($X_4X_3X_2X_1$) immediately N-terminal to said KEX2 site.

In yet other embodiments, the invention relates to a process of producing a desired protein in a filamentous fungal host cell and particularly in a *Trichoderma* cell, comprising obtaining a filamentous fungal host cell comprising a fusion DNA construct according to the invention and culturing the filamentous fungal host cell under suitable conditions which allow the expression and secretion of the desired protein. In some aspects of this embodiment, the desired protein will be recovered. In other aspects of this embodiment, the cleavage of the desired protein from the fusion polypeptide will be greater than the cleavage of the same desired protein from an equivalent fusion polypeptide that lacks the KEX2 site pre-sequence. In other aspects of this embodiment, the secretion of the desired protein from the fusion polypeptide will be greater than the secretion of the same desired protein from an equivalent fusion polypeptide, which lacks the KEX2 site pre-sequence.

In an additional embodiment, the invention relates to a method for identifying enhanced secretion and/or cleavage of a desired protein comprising a) altering a KEX2 site pre-sequence of a parental fusion polypeptide, said parental fusion polypeptide comprising a signal sequence; a KEX2 region comprising a KEX2 site and the KEX2 site pre-sequence which is located immediately N-terminal to said KEX2 site, and an amino acid sequence comprising a desired protein to produce a set of test fusion polypeptides that are identical to said parental fusion polypeptide except for said KEX2 site pre-sequence; b) evaluating secretion of said test fusion polypeptides and said parental fusion polypeptide by a filamentous fungal cell; c) identifying a test fusion polypeptide that has enhanced secretion and/or cleavage as compared to said parental fusion polypeptide.

In further aspects of this embodiment, the invention relates to a method of identifying an optimized KEX2 site pre-sequence which comprises, testing a plurality of different test fusion polypeptides obtained as described above; and determining which of said different test fusion polypeptides has greater secretion and/or protein cleavage, wherein said optimized KEX2 site pre-sequence is the altered KEX2 site pre-sequence of the test fusion polypeptide that has the greatest secretion and/or protein cleavage.

BRIEF DESCRIPTION OF THE FIGURES

Certain aspects of the following detailed description are best understood when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 3A-E provide the nucleotide sequence (SEQ ID NO: 103) (10885 bp) of the pTrex4-her2 light chain DNA2.0 plasmid of FIG. 2.

DEFINITIONS

Figure 1:
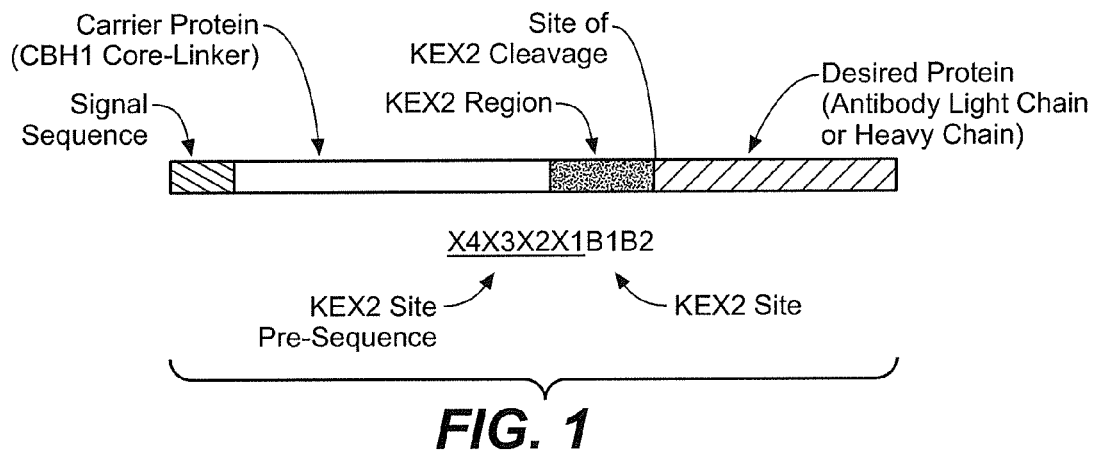
FIG. 1 schematically illustrates an embodiment of a fusion polypeptide according to the invention, including a carrier protein, a KEX2 region and a desired protein, wherein the carrier protein is illustrated as a cellobiohydrolase I (CBH1) core/linker, which comprises the catalytic domain and part of the linker region of the CBH1 protein and the desired protein is illustrated as an antibody light chain or heavy chain.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express nucleic acids or polypeptides that are not found within the native (non-recombinant) form of the cell or express native genes that are otherwise abnormally expressed, under expressed, over expressed or not expressed at all.

A "gene" refers to a DNA segment that is involved in producing a polypeptide and includes regions preceding and following the coding regions, e.g., the promoter and terminator, as well as intervening sequences (introns) between individual coding segments (exons).

The term "nucleic acid" encompasses DNA, RNA, single stranded or double stranded and chemical modifications thereof. The terms "nucleic acid" and "polynucleotide" may be used interchangeably herein. Because the genetic code is degenerate, more than one codon may be used to encode a particular amino acid, and the present invention encompasses polynucleotides, which encode a particular amino acid sequence.

The term "DNA construct" means a DNA sequence which is operably linked to a suitable control sequence capable of effecting expression of a protein in a suitable host. Such control sequences may include a promoter to effect transcription, an optional operator sequence to control transcription, a sequence encoding suitable ribosome binding sites on the mRNA, enhancers and sequences which control termination of transcription and translation.

The term "fusion DNA construct" or "fusion nucleic acid" refers to a nucleic acid which comprises from 5' to 3' a number of polynucleotide sequences (e.g. a DNA molecule encoding a signal sequence, a DNA molecule encoding a carrier protein, a DNA molecule coding for a KEX2 site and a DNA molecule encoding a desired protein) operably linked together and which encode a fusion polypeptide.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a vector that has the ability to incorporate and express heterologous DNA fragment in a foreign cell. Many prokaryotic and eukaryotic expression vectors are commercially available.

A "promoter" is a regulatory sequence that is involved in binding RNA polymerase to initiate transcription of a gene.

The term "signal sequence" refers to a sequence of amino acids at the amino terminus of a protein that directs the protein to the secretion system for secretion from a cell. The signal sequence is cleaved from the protein prior to secretion of the protein. In certain cases, a signal sequence may be referred to as a "signal peptide" or "leader peptide". The definition of a signal sequence is a functional one. The mature form of the extracellular protein lacks the signal sequence which is cleaved off during the secretion process.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process which occurs after mRNA has been formed.

The term "operably linked" refers to juxtaposition wherein the elements are in an arrangement allowing them to be functionally related. For example, a promoter is operably linked to a coding sequence if it controls the transcription of the sequence.

The term "selective marker" refers to a protein capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

The terms "protein" and "polypeptide" are used interchangeably herein. The conventional one-letter or three-letter code for amino acid residues is used herein.

The term "carrier protein" refers to a polypeptide sequence or functional portion thereof from a naturally secreted fungal polypeptide.

The term "antibody protein" used interchangeably with immunoglobulins (Igs), refers to a protein containing one or more polypeptides that specifically binds an antigen. Included by this term are antibodies of any isotype, fragments of antibodies which retain specific binding to antigen, including, but not limited to, Fab, Fv, scFv, Fd, Fab', Fv, F(ab')$_2$ antibodies, antibody fragments that retain specific binding to antigen, monoclonal antibodies, chimeric antibodies, humanized antibodies, single-chain antibodies, bi-functional (i.e. bi-specific) hybrid antibodies and fusion proteins comprising an antigen-binding portion of an antibody and a non-antibody protein.

The monomeric form of an antibody comprises four polypeptide chains of two different types, one heavy and one light. Different types of heavy and light chains are recognized. The light chains are structurally divided into two domains, a variable region (VL) and a constant region (CL). The heavy chain is also divided into distinct structural domains. For example, a γ heavy chain comprises, from the amino terminus, a variable region (VH), a constant region (CH1), a hinge region, a second constant region (CH2) and a third constant region (CH3).

The term "equivalent fusion polypeptide" refers to a fusion polypeptide which has an identical amino acid sequence compared to a reference fusion polypeptide, except for a KEX2 site pre-sequence. A first fusion polypeptide having a first KEX2 site pre-sequence is equivalent to a second fusion polypeptide having a different KEX2 site pre-sequence if the polypeptides have identical amino acid sequences, except for the difference in the KEX2 site pre-sequence.

The term "derived" encompasses the terms "originated from", "obtained" or "obtainable from", and "isolated from".

"Host strain" or "host cell" means a suitable host for an expression vector or DNA construct comprising a polynucleotide encoding a polypeptide and particularly a recombinant fusion polypeptide encompassed by the invention. In specific embodiments, the host strains may be a filamentous fungal cell. The term "host cell" includes both cells and protoplasts.

The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, glucans, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic.

The term "culturing" refers to growing a population of microbial cells under suitable conditions in a liquid or solid medium.

The term "heterologous" with reference to a polynucleotide or polypeptide refers to a polynucleotide or polypeptide that does not naturally occur in a host cell. In some embodiments, the protein is a commercially important industrial protein and in some embodiments, the heterologous protein is a therapeutic protein. It is intended that the term encompass proteins that are encoded by naturally occurring genes, mutated genes, and/or synthetic genes.

The term "homologous" with reference to a polynucleotide or protein refers to a polynucleotide or protein that occurs naturally in the host cell.

The terms "recovered", "isolated", and "separated" as used herein refer to a protein, cell, nucleic acid or amino acid that is removed from at least one component with which it is naturally associated.

As used herein, the terms "transformed", "stably transformed" and "transgenic" used in reference to a cell means the cell has a non-native (e.g., heterologous) nucleic acid sequence or additional copy of a native (e.g., homologous) nucleic acid sequence integrated into its genome or has an episomal plasmid that is maintained through multiple generations.

As used herein, the term "expression" refers to the process by which a polypeptide is produced based on the nucleic acid sequence of a gene. The process includes both transcription and translation.

The term "glycosylated" protein means a protein that has oligosaccharide molecules added to particular amino acid residue on the protein.

The term "non-glycosylated" protein is a protein that does not have oligosaccharide molecules attached to the protein.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "KEX2" refers to a calcium-dependent endopeptidase having an activity defined as EC 3.4.21.61, according to IUBMB Enzyme Nomenclature. KEX2 cleaves a peptide bond (the KEX2 cleavage site) that is immediately C-terminal to a pair of basic amino acids during protein secretion.

The term "KEX2 region" refers to a contiguous eight to four amino acid residue region which is located between the C-terminus end of a carrier protein and the N-terminal end of a desired protein in a fusion polypeptide. The KEX2 region is comprised of a KEX2 site and a KEX2 site pre-sequence.

The term "KEX2 site" refers to a two amino acid KEX2 cleavage motif in a protein. A KEX2 site contains two contiguous basic amino acids (e.g., lysine, histidine and/or arginine) in any order, (e.g., KK, RR, KR or RK).

The term "KEX2 site pre-sequence" refers to the two to six contiguous amino acids $[(X)_n$ where n is 2 to 6] immediately preceding (i.e., immediately N-terminal to) the KEX2 site. For example, if a KEX2 region is defined as VAVEKR, the "KR" motif is the KEX2 site of the region; n is 4 and the "VAVE" motif corresponds to the KEX2 site pre-sequence of the region.

The term "variant" refers to a region of a protein that contains one or more different amino acids as compared to a reference protein.

The term "secreted protein" refers to a region of a polypeptide that is released from a cell during protein secretion. In some embodiments, the secreted protein is the protein that is released or cleaved from a recombinant fusion polypeptide of the invention.

The term "secretion" refers to the selective movement of a protein across a membrane in a host cell to the extracellular space and surrounding media.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute.

"Assessing the presence of" includes determining the amount of something present, as well as determining whether it is present or absent.

Other definitions of terms may appear throughout the specification.

DETAILED DESCRIPTION

Before the exemplary embodiments are described in more detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Although any methods and materials similar or equivalent to those described herein can be used in the practice or testing of the present invention, exemplary and preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Fusion Polypeptides—

As noted above, the subject fusion polypeptide comprises: a) a signal sequence; b) a carrier protein; c) a KEX2 region comprising: i) a KEX2 site and ii) a KEX2 site pre-sequence immediately N-terminal to the KEX2 site; and d) a desired protein.

FIG. 1 illustrates a subject fusion polypeptide of the invention. The various parts of a subject polypeptide (i.e., "signal sequence", carrier protein, "KEX2 region" and "desired protein") are so labeled solely for clarity and convenience. It is recognized that the subject fusion polypeptide may also be referred to as a "pro-protein" or "precursor protein" because it generally contains an N-terminal region that is cleaved off during secretion and a C-terminal region that is secreted.

Signal Sequences and Carrier Proteins—

The signal sequence of a subject fusion polypeptide may be any signal sequence that facilitates protein secretion from a filamentous fungal cell. In particular embodiments, the subject fusion polypeptide may comprise a signal sequence for a protein that is known to be highly secreted from the filamentous cell in which the fusion protein is to be produced. The signal sequence employed may be endogenous or non-endogenous to the cell in which the fusion polypeptide is to be produced. In particular embodiments, the signal sequence may comprise a "carrier" that contains the signal sequence at its N-terminus, where the carrier is at least an N-terminal portion of a protein that is endogenous to the cell and efficiently secreted by a cell.

Suitable signal sequences and carriers are known in the art (see, e.g., Ward et al, Bio/Technology 1990 8:435-440; and Paloheimo et al, Applied and Environmental Microbiology 2003 69: 7073-7082). Examples of suitable signal sequences and carrier proteins include those of cellobiohydrolase I, cellobiohydrolase II, endoglucanases I, II and III, α-amylase, aspartyl proteases, glucoamylase, phytase, mannanase, α and β glucosidases, bovine chymosin, human interferon and human tissue plasminogen activator and synthetic consensus eukaryotic signal sequences such as those described by Gwynne et al., (1987) Bio/Technology 5:713-719.

In some embodiments, if Trichoderma (e.g. T. reesei) is employed as a host cell, the signal sequence or carrier of T. reesei mannanase I (Man5A, or MANI), T. reesei cellobiohydrolase II (Cel6A or CBHII), endoglucanase I (Cel7b or EGI), endoglucanase II (Cel5a or EGII), endoglucanase III (Cel12A or EGIII), xylanases I or II (XynIIa or XynIIb) or T. reesei cellobiohydrolase I (Cel7a or CBHI) may be employed in the fusion polypeptide.

In other embodiments, if an Aspergillus (e.g. A. niger) is employed as a host cell, the signal sequence or carrier of A. niger glucoamylase (GlaA) or alpha amylase may be employed in the fusion polypeptide. Aspergillus niger and Aspergillus awamori glucoamylases have identical amino acid sequences. Two forms of the enzyme are generally recognized in culture supernatants. GAI is the full length form (amino acid residues 1-616) and GAII is a natural proteolytic fragment comprising amino acid residues 1-512. GAI is known to fold as two separate domains joined by an extended linker region. The two domains are the 471 residue catalytic domain (amino acids 1-471) and the 108 residue starch binding domain (amino acids 509-616), the linker region between the two domains being 36 residues (amino acids 472-508). GAII lacks the starch binding domain. Reference is made to Libby et al., (1994) Protein Engineering 7:1109-1114. In some embodiments, the glucoamylase which is used as a carrier protein and including a signal sequence will have greater than 95%, 96%, 97%, 98% and 99% sequence identity with a catalytic domain of an Aspergillus or Trichoderma glucoamylase. The term "catalytic domain" refers to a structural portion or region of the amino acid sequence of a protein which posses the catalytic activity of the protein.

In certain embodiments, the signal sequence and the carrier protein are obtained from the same gene. In some embodiments, the signal sequence and the carrier protein are obtained from different genes.

The carrier protein may include all or part of the mature sequence of a secreted polypeptide. In some embodiments, full length secreted polypeptides are used. However, functional portions of secreted polypeptides may be employed. As used herein "portion" of a secreted polypeptide or grammatical equivalents means a truncated secreted polypeptide that retains its ability to fold into a normal, albeit truncated, configuration.

In some cases, the truncation of the secreted polypeptide means that the functional protein retains a biological function. In some embodiments, the catalytic domain of the secreted polypeptide is used, although other functional domains could be used, for example the substrate binding domain. In one embodiment, when glucoamylase is used as the carrier protein (i.e. glucoamylase from Aspergillus niger), preferred functional portions retain the catalytic domain of the enzyme and include amino acids 1-471 (see, WO 03089614, e.g., example 10). In another embodiment, when CBH I is used as the carrier protein (i.e. CBH I from Trichoderma reesei) preferred functional portions retain the catalytic domain of the enzyme. Reference is made to SEQ ID NO:1 of FIG. 2 of WO 05093073, wherein the sequence encoding a Trichoderma reesei CBH1 signal sequence, T. reesei CBH1 catalytic domain (also referred to as catalytic core or core domain) and T. reesei CBH1 linker is disclosed. In some embodiments, a CBH1 carrier protein and including a signal sequence will have greater than 95%, 96%, 97%, 98% and 99% sequence identity with SEQ ID NO:1 of FIG. 2 of WO 05093073.

In general, if the carrier protein is a truncated protein, it is C-terminally truncated (i.e., contains an intact N-terminus). Alternatively, the carrier protein may be N-terminally truncated, or optionally truncated at both ends to leave a functional portion. Generally such portions of a secreted protein which comprise a carrier protein comprise greater than 50%, greater than 70%, greater than 80% and greater than 90% of the secreted protein and preferably the N-terminal portion of the secreted protein. In some embodiments, the carrier protein will include a linker region in addition to the catalytic domain. In the fusion constructs of the examples herein, part of the linker region of the CBHI protein was used in the carrier protein.

As used herein, the first amino acid sequence comprising a signal sequence functional as a secretory sequence is encoded by a first DNA molecule. The second amino acid sequence comprising the carrier protein is encoded by a second DNA sequence. However, as described above the signal sequence and the carrier protein may be obtained from the same gene.

KEX2 Region—

The KEX2 region comprises a KEX2 site ($B_1B_2$) and a KEX2 site pre-sequence (($X)_{n=2-6}$) immediately N-terminal to said KEX2 site. In some embodiments the KEX2 region provides means for cleavage (separation) at the amino terminus of the desired protein from the fusion polypeptide in vivo. The KEX2 region of a fusion polypeptide of the encompassed by the invention is not a naturally occurring region between the carrier protein and the desired protein.

The KEX2 cleavage site, which occurs at the C-terminal end of the KEX2 region, may be cleaved by a native filamentous fungal protease (e.g. a native *Aspergillus* KEXB-like protease or native *Trichoderma* KEX2 protease). The desired protein is cleaved from a fusion polypeptide according to the invention immediately downstream of the KEX2 site.

The KEX2 site contains amino acid sequence "$B_1B_2$" wherein $B_1$ and $B_2$, are independently, basic amino acids. Preferably the KEX2 site includes any one of KK, KR, RK or RR and more preferably is KR.

The KEX2 site pre-sequence comprises amino acid sequence $(X)_{n=2-6}$ wherein X is any amino acid and n is 2 to 6 and preferably 4. The KEX2 region as defined herein is not found naturally in the carrier protein at the C-terminus of the carrier protein, which comprises the fusion polypeptide according to the invention. In some embodiments, the KEX2 site pre-sequence is an amino acid sequence that is different from the naturally occurring contiguous $(X)_{n=2-6}$ amino acid residues on the C-terminus of the carrier protein. However, the contiguous $(X)_{n=2-6}$ amino acid residues may be found in other parts of the carrier protein and may be linked with a KEX2 site ($B_1B_2$) but the KEX2 region will not be attached to the N-terminus of the desired protein.

In some embodiments, when the KEX2 site pre-sequence is defined as $X_4X_3X_2X_1B_1B_2$,
  a) $X_1$, $X_2$ and $X_3$ are not G;
  b) $X_1$ is not S, if $X_2$ and $X_3$ are G, $X_4$ is A, or $X_3$ is S;
  C) $X_4$ is not T, if $X_3$ is A and $X_2$ is S; or
  d) $X_1$ is not D.

In some preferred embodiments, the KEX2 region is $X_4X_3X_2X_1B_1B_2$ wherein $B_1B_2$ is KR and
  a) $X_1$, $X_2$ and $X_3$ are not G;
  a) $X_1$ is not S, if $X_2$ and $X_3$ are G, $X_4$ is A, or $X_3$ is S;
  b) $X_4$ is not T, if $X_3$ is A and $X_2$ is S; or
  c) d) $X_1$ is not D.

In other embodiments, the KEX2 site pre-sequence is defined as $X_4X_3X_2X_1$ wherein,
  a) $X_4$ is V, S, N, L, or K;
  a) $X_3$ is A, V, D, W, E or P;
  b) $X_2$ is V, I, L or F; and
  c) $X_1$ is E, S, T or Y.

In yet other embodiments the KEX2 site pre-sequence is defined as $X_4X_3X_2X_1$ wherein,
  a) $X_4$ is V, N, or L;
  a) $X_3$ is A, V, D, W, E or P;
  b) $X_2$ is V, I, L or F; and
  c) $X_1$ is E or Y.

In yet further embodiments the $X_4X_3X_2X_1$KR KEX2 region may be selected from the group of $X_4$ is V; $X_3$ is A; $X_2$ is V; $X_1$ is E or Y and combinations thereof.

In some embodiments, the KEX2 site pre-sequence is selected from the group consisting of VAVE (SEQ ID NO: 84); NVIS (SEQ ID NO: 85); SDVT (SEQ ID NO: 86); VAVY (SEQ ID NO: 87); LAVE (SEQ ID NO: 88); KAVE (SEQ ID NO: 89); VAIE (SEQ ID NO: 90); VALE (SEQ ID NO: 91); VAFE (SEQ ID NO: 92); VWVE (SEQ ID NO: 93); VEVE (SEQ ID NO: 94); and VPVE (SEQ ID NO: 95).

In some embodiments, the KEX2 site pre-sequence is not KSRS (SEQ ID NO: 109); SRIS (SEQ ID NO: 111); GGGS (SEQ ID NO: 110); TSTY (SEQ ID NO: 96); ASIS (SEQ ID NO: 97); ATAS (SEQ ID NO: 98); TASQ (SEQ ID NO: 99); TASL (SEQ ID NO: 100), SVIS (SEQ ID NO: 101); NVIS (SEQ ID NO: 85); GGG; TSRD (SEQ ID NO: 102); SPMD (SEQ ID NO: 106); DLGE (SEQ ID NO: 107); or TPTA (SEQ ID NO: 108).

While the preferred KEX2 region is defined as $X_4X_3X_2X_1B_1B_2$, as indicated above, the KEX2 site pre-sequence can include 6 amino acid residues, in some embodiments, the KEX2 region may include one or two more amino acid residues In other embodiments, the KEX2 site pre-sequence may include only 2 or 3 amino acid residues ($X_3X_2X_1B_1B_2$ or $X_2X_1B_1B_2$). In this embodiment,
  a) $X_1$, $X_2$ and $X_3$ are not G (e.g. GGGB$_1$B$_2$ or GGB$_1$B$_2$),
  a) $X_1$ is not S, if $X_2$ and $X_3$ are G or $X_3$ is S (e.g. SX$_2$S or SGS); and
  b) $X_1$ is not D.

In some embodiments, the KEX2 site pre-sequence provides for enhanced cleavage and/or secretion of a desired protein from a host cell as compared to the cleavage and/or secretion of the desired protein from an equivalent fusion polypeptide lacking a KEX2 site pre-sequence.

In some embodiments, the KEX2 site pre-sequence is an optimized KEX2 site pre-sequence. An optimized KEX2 pre-sequence is a KEX2 pre-sequence encompassed by the invention but which provides greater or more efficient cleavage or secretion from a host cell as compared to other variant KEX2 site pre-sequences.

In some embodiments, the fusion polypeptide encompassed by the invention will include an optimized KEX2 pre-sequence as the KEX2 pre-sequence. The optimized KEX2 pre-sequence may be employed with any signal sequence, any carrier region from a secreted protein, any KEX2 site, or any desired protein. A subject KEX2 region containing an optimized KEX2 site pre-sequence may be non-naturally occurring. In certain embodiments, a subject KEX2 region containing an optimized KEX2 site pre-sequence is not found in any protein that is secreted from a filamentous fungal cell.

Desired Proteins—

The desired protein (or the carrier protein) may be any portion of a protein that can be secreted from a filamentous fungal cell, which proteins include, so called industrial enzymes, therapeutic proteins, hormones, structural proteins, plasma proteins, food additives and foodstuffs and the like. The desired protein may be a heterologous or homologous protein and may include hybrid polypeptides that comprise a combination of partial or complete polypeptides each of which may be homologous or heterologous with regard to the fungal expression host. The desired secreted protein may be derived from bacterial (e.g. *Bacillus* species and *Pseudomonas* species) fungal (e.g. *Aspergillus, Trichoderma, Humicola*, or *Mucor* species), viral (e.g. Hepatitis A or B or Adenovirus), mammalian (e.g. human or mouse), and plant sources. Desired proteins include naturally occurring allelic variations of proteins as well as engineered variations.

In one embodiment, the desired protein may be an enzyme such as a carbohydrase, such as a starch hydrolyzing α-amylase, an alkaline α-amylase, a β-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, bromelain, ficin, a neutral protease, papain, pepsin, a peptidase, rennet, rennin, chymosin, subtilisin, thermolysin, an aspartic proteinase, or trypsin; a granular starch hydrolyzing enzyme, such as a glucoamylase or an alpha amylase; a lipase or esterase, such as a triglyceridase, a phospholipase, a pregastric esterase, a phosphatase, a phytase, an amidase, an iminoacylase, a glutaminase, a lysozyme, or a penicillin acylase; an isomerase such as glucose isomerase; a phenol oxidizing enzyme, e.g., a laccase; an oxidoreductases, e.g., an amino acid oxidase, a catalase, a chloroperoxidase, a glucose oxidase, a hydroxysteroid dehydrogenase or a peroxidase; a lyase such as a acetolactate decarboxylase, a aspartic β-decarboxylase, a fumarese or a histadase; a transferase such as cyclodextrin glycosyltranferase or an acyl transferase; or a ligase, for example. In particular embodiments, the protein may be an aminopeptidase, a carboxypeptidase, a chitinase, a glucoamylase, an alpha amylase, a cutinase, a phytase, a deoxyribonuclease, an α-galactosidase, a β-galactosidase, a β-glucosidase, a laccase, a mannosidase, a mutanase, a pectinolytic enzyme, a polyphenoloxidase, ribonuclease or transglutaminase.

In other embodiments, the desired protein may be a therapeutic protein (i.e., a protein having a therapeutic biological activity). Examples of suitable therapeutic proteins include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, immunoglobulin, such as immunoglobulin G (IgG), IgG fragments, IgG fusions, IgM or IgA; interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist.

In some preferred embodiments, the desired protein is an immunoglobulin from any class, G, A, M, E or D. (See, U.S. Pat. No. 4,816,567 and references cited therein for a discussion of immunoglobulin structure). In other preferred embodiments, the antibody proteins such as monoclonal antibodies including heavy or light chains and fragments thereof. In further embodiments, humanized antibodies are of particular interest as a desired protein (e.g. trastuzumab (herceptin)). Some specific examples of preferred monoclonal antibody fragments are truncated forms of the heavy chain to remove part of the constant region such as Fab fragments in which the heavy chain (Fd) lacks the hinge region and the CH2 and CH3 domains; Fab' fragments in which the heavy chain includes the hinge region but lacks the CH2 and CH3 domains; and F(ab')$_2$ fragments which includes the Fab portion connected by the hinge region. (Verma et al., (1998) J. Immunological Methods 216:165-181 and Pennell and Eldin (1998) Res. Immunol. 149:599-603). Also of interest are single chain antibodies (ScFv) and single domain antibodies (e.g., camelid antibodies).

In some particularly preferred embodiments a fusion polypeptide according to the invention will comprise in operable linkage a signal sequence; a carrier protein; a KEX2 region and a desired protein as indicated below:

Fusion DNA Constructs and Vectors—

In some embodiments, the invention provides a fusion DNA construct encoding a fusion polypeptide as disclosed above, comprising in operable linkage from the 5' end of said construct, a promoter; a first DNA molecule encoding a signal sequence; a second DNA molecule encoding a carrier protein; a third DNA molecule encoding a KEX2 region, said KEX2 region comprising a KEX2 site and a KEX2 site pre-sequence immediately 5' to the KEX2 site; and a fourth DNA molecule encoding a desired protein. Since the genetic code is known, the design and production of these nucleic acids is well within the skill of an artisan, given the description of the subject fusion polypeptide. In certain embodiments, the nucleic acids may be codon optimized for expression of the fusion polypeptide in a particular host cell. Since codon usage tables are available for many species of filamentous fungi, the design and production of codon-optimized nucleic acids that encodes a subject fusion polypeptide would be well within the skill of one of skill in the art.

Promoters—

Examples of suitable promoters for directing the transcription of a subject nucleic acid in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase (Korman et al (1990) Curr. Genet. 17:203-212; Gines et al., (1989) Gene 79: 107-117), *Aspergillus niger* or *Aspergillus awamori* glucoamylase (glaA) (Nunberg et al., (1984) Mol. Cell. Biol. 4:2306-2315; Boel E. et al., (1984) EMBO J. 3: 1581-1585), *Rhizomucor miehei* lipase, *Aspergillus oryzae* alkaline protease, *Aspergillus oryzae* triose phosphate isomerase, *Aspergillus nidulans* acetamidase (Hyner et al., (1983) Mol. Cell. Biol. 3:1430-1439), *Fusarium venenatum* amyloglucosidase, *Fusarium oxysporum* trypsin-like protease (WO 96/00787), *Trichoderma reesei* cellobiohydrolase I (Shoemaker et al. (1984) EPA EPO 0137280), *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof. Reference is also made to Yelton et al., (1984) Proc. Natl. Acad. Sci. USA 81:1470-1474; Mullaney et al., (1985) Mol. Gen. Genet. 199:37-45; Lockington et al., (1986) Gene 33: 137-149; Macknight et al., (1986) Cell 46: 143-147; Hynes et al., (1983) Mol. Cell. Biol. 3: 1430-1439. Higher eukaryotic promoters such as SV40 early promoter (Barclay et al (1983) Molecular and Cellular Biology 3:2117-2130) may also be useful. Promoters may be constitutive or inducible promoters. Some preferred promoters include a *Trichoderma reesei* cellobiohydrolase I or II, a *Trichoderma reesei* endoglucanase I, II or III, and a *Trichoderma reesei* xylanase H.

Vectors—

A subject polynucleotide may be present in a vector, for example, a phage, plasmid, viral, or retroviral vector. In certain embodiments, the vector may be an expression vector for expressing a subject fusion polypeptide in a filamentous fungal cell.

Vectors for expression of recombinant proteins are well known in the art (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.).

A fusion DNA construct according to the invention may be constructed using well known techniques as is generally described for example in EPO publication 0 215 594.

Natural or synthetic polynucleotide fragments encoding for the desired protein (e.g. an immunoglobulin) may be incorporated into heterologous nucleic acid constructs or vectors, capable of introduction into and replication in a filamentous fungal cell.

Once a DNA construct or more specifically a fusion DNA construct encompassed by the invention is made it may be incorporated into any number of vectors as is known in the art. While the DNA construct will preferably include a promoter sequence, in some embodiments the vector will include other regulatory sequences functional in the host to be transformed, such as ribosomal binding sites, transcription start and stop sequences, terminator sequences, polyadenylation signals, enhancers and or activators. In some embodiments, a polynucleotide encoding the desired protein and KEX2 region will be inserted into a vector which comprises a promoter, signal sequence and carrier protein at an appropriate restriction endonuclease site by standard procedures. Such procedures and related sub-cloning procedures are deemed to be within the scope of knowledge of those skilled in the art.

Terminator sequences which are recognized by the expression host to terminate transcription may be operably linked to the 3' end of the fusion DNA construct encoding the fusion protein to be expressed. Those of general skill in the art are well aware of various terminator sequences that may be used with filamentous fungi. Non-limiting examples include the terminator from the *Aspergillus nidulans* trpC gene (Yelton M. et al., (1984) Proc. Natl. Acad. Sci. USA 81: 1470-1474) or the terminator from the *Aspergillus niger* glucoamylase genes (Nunberg et al. (1984) Mol. Cell. Biol. 4: 2306-2353) or the terminator from the *Trichoderma reesei* cellobiohydrolase I gene.

Polyadenylation sequences are DNA sequences which when transcribed are recognized by the expression host to add polyadenosine residues to transcribed mRNA. Examples include polyadenylation sequences from *A. nidulans* trpC gene (Yelton et al (1984) Proc. Natl. Acad. Sci. USA 81; 1470-1474); from *A. niger* glucoamylase gene (Nunberg et al. (1984) Mol. Cell. Biol. 4:2306-2315); the *A. oryzae* or *A. niger* alpha amylase gene and the *Rhizomucor miehei* Carboxyl protease gene. Any fungal polyadenylation sequence is likely to be functional in the present invention.

In further embodiments, the fusion DNA construct or the vector comprising the fusion DNA construct will contain a selectable marker gene to allow the selection of transformed host cells. Selection marker genes are well known in the art and will vary with the host cell used. Examples of selectable markers include but are not limited to ones that confer antimicrobial resistance (e.g. hygromycin, bleomycin, chloroamphenicol and phleomycin). Genes that confer metabolic advantage, such as nutritional selective markers also find use in the invention. Some of these markers include amdS. Also sequences encoding genes which complement an auxotrophic defect may be used as selection markers (e.g. pyr4 complementation of a pyr4 deficient *A. nidulans*, *A. awamori* or *Trichoderma reesei* and argB complementation of an argB deficient strain). Reference is made to Kelley et al., (1985) EMBO J. 4: 475-479; Penttila et al., (1987) Gene 61:155-164 and Kinghorn et al (1992) Applied Molecular Genetics of Filamentous Fungi, Blackie Academic and Professional, Chapman and Hall, London.

Host Cells—

A host cell comprising a fusion DNA construct according to the invention is also provided. In certain embodiments, the host cell may be a filamentous fungal host cell. In some embodiments, the cells may be filamentous fungal cells of a strain that has a history of use for production of proteins that have GRAS status, i.e., a Generally Recognized as Safe, by the FDA.

In particular embodiments, the subject fungal cell may be a cell of the following species: *Trichoderma*, (e.g., *Trichoderma reesei* (previously classified as *T. longibrachiatum* and currently also known as *Hypocrea jecorina*), *Trichoderma viride*, *Trichoderma koningii*, and *Trichoderma harzianum*)); *Penicillium* sp.: *Humicola* sp. (e.g., *Humicola insolens* and *Humicola grisea*); *Chrysosporium* sp. (e.g., *C. lucknowense*); *Gliocladium* sp.; *Aspergillus* sp. (e.g., *Aspergillus oryzae*, *Aspergillus niger*, *Aspergillus nidulans*, *Aspergillus kawachi*, *Aspergillus aculeatus*, *Aspergillus japonicus*, *Aspergillus sojae*, and *Aspergillus awamori*), *Fusarium* sp.; *Mucor* sp.; *Neurospora* sp.; *Hypocrea* sp.; or *Emericella* sp. (See also, Innis et al., (1985) Sci. 228:21-26), among others. In some embodiments, subject fungal cells may be strains of *Aspergillus oryzae*, ATCC 11490, *Aspergillus niger* which include ATCC 22342, ATCC 44733, ATCC 14331, NRRL 3112, and strains derived therefrom. In some embodiments, subject fungal cells may be strains of *Trichoderma* which include functional equivalents of RL-P37 (Sheir-Neiss et al. (1984) *Appl. Microbiol. Biotechnology* 20:46-53). Useful *Trichoderma* host strains include; NRRL 15709, ATCC 13631, ATCC 26921 (QM 9414) ATCC 32098, ATCC 32086, and ATCC 56765 (RUTC-30).

In some embodiments, a host cell may be one wherein native genes have been deleted or inactivated. In some embodiments, preferred host cells have inactivated protease genes (e.g. aspartyl protease) and reference is made to Berka et al. (1990) Gene 86:153-162 and U.S. Pat. No. 6,509,171. In some embodiments, preferred host cells have inactivated cellulase genes (e.g. cbh1, cbh2 and egl1, and egl2) and reference is made to the quad deleted strain of *T. reesei* disclosed in WO 05/001036.

The above described fusion DNA construct may be present in the nuclear genome of the host cell or may be present in a plasmid that replicates in the host cell, for example.

Transformation

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) *Curr. Genet.* 16:53-56). Reference is also made to WO 05/001036; U.S. Pat. No. 6,022,725; U.S. Pat. No. 6,103,490; U.S. Pat. No. 6,268,328; [and published U.S. patent applications 20060041113, 20060040353, 20060040353 and 20050208623], which publications are incorporated herein by reference.

The expression of recombinantly introduced proteins in *Trichoderma* is described in U.S. Pat. No. 6,022,725; U.S. Pat. No. 6,268,328; Harkki et al. (1991); *Enzyme Microb.*

Technol. 13:227-233; Harkki et al., (1989) *Bio Technol.* 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Reference is also made to Cao et al., (2000) Protein Sci. 9:991-1001; Yelton et al., (1984) Proc. Natl. Acad. Sci. 81:1470-1471; U.S. Pat. No. 6,590,078; and Berka, et al., (1991) in: Applications of Enzyme Biotechnology, Eds. Kelly and Baldwin, Plenum Press, NY) for transformation of *Aspergillus* strains.

In one embodiment, the preparation of *Trichoderma* sp. for transformation involves the preparation of protoplasts from fungal mycelia. (See, Penttila et al., (1987) Gene 61:155-164). In some embodiments, the mycelia are obtained from germinated vegetative spores.

Generally, cells are cultured in a standard medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth also find use in the present invention. Preferred culture conditions for a given filamentous fungus are known in the art and may be found in the scientific literature and/or from the source of the fungi such as the American Type Culture Collection (ATCC) and Fungal Genetics Stock Center.

In some embodiments, when an immunoglobulin is the desired protein immunoglobulin expressing cells will be cultured under conditions typically employed to culture the parental cell line. Generally, cells will be cultured in standard medium containing physiological salts and nutrients such as that described by Ilmen et al., (1997) supra. Culture conditions will also be standard (e.g. incubation at 25-30° C. in shake flasks on a rotary shaker) until desired levels of immunoglobulin expression is achieved.

Protein Production Methods

Methods of producing a desired protein in a filamentous fungal cell are also encompassed by the invention. In some embodiments these methods include, obtaining a filamentous host cell comprising a fusion DNA construct or vector according to the invention and culturing the filamentous host cell under suitable conditions which allow the expression and secretion of the desired protein. While a culture of host cells (i.e., a composition containing subject host cells and growth media) may contain the secreted protein of the fusion polypeptide described above, in some embodiments the desired protein is recovered from the culture media. In other embodiments, the desired protein is purified. Protein may be recovered from growth media by any convenient method.

In some embodiments, a subject fungal cell may be cultured under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are known.

Expression and Secretion—

The production of a desired protein in a filamentous fungal cell comprising a fusion DNA construct encoding a fusion polypeptide results in the secretion of the desired protein of the fusion polypeptide. During the secretion process in fungi, sugar chains may be attached to a protein to be secreted to produce a glycosylated protein. In the present invention, the production of the desired protein, (e.g. an antibody), may include glycosylated or non-glycosylated protein.

In some embodiments, the secreted protein of the subject fusion polypeptide is generally present in the culture medium of the filamentous fungal cell at an amount that is higher than the amount of the desired secreted protein of an equivalent fusion polypeptide that lacks the KEX2 site pre-sequence, produced by an equivalent filamentous fungal cell (i.e., the same cell type, grown under the same conditions). A culture of the subject cells producing a desired protein from a fusion polypeptide according to the invention may contain more than 5%, more than 10%, more than 20%, more than 40%, more than 60%, more than 80%, more than 100%, more than 150%, more than 200%, more than 300%, more than 500%, and more than 1000% desired protein in the growth medium, as compared to an equivalent cell culture that expresses an otherwise equivalent protein that does not have a KEX2 site pre-sequence as encompassed by the invention.

In some embodiments, the level of expression and secretion for a desired protein (e.g. a full-length antibody) will be greater than 0.5 g/L. Routinely greater than 1.0 g/L of the desired protein may be recovered from a culture media. Reproducible levels of greater than 1.5, 2.0 and 3.0 g/L may be attained. In some embodiments, the level of expression and secretion of the desired protein will be greater than 10 g/L and even greater than 20 g/L.

In some embodiments of the invention, the cleavage of the desired protein from the recombinant fusion polypeptide will be greater than the cleavage of the same desired protein from an equivalent recombinant fusion polypeptide which lacks the KEX2 site pre-sequence. In some embodiments, the KEX2 site pre-sequence may result in a fusion protein that is cleaved to at least 80%, at least 85%, at least 90%, at least 95%, at least 97%, at least 98%, at least 99% or 100% efficiency, wherein 100% efficiency results in a completely cleaved desired secretion protein from the fusion polypeptide.

In certain embodiments, the efficiency of protein cleavage may be calculated by determining amount of cleavage that has occurred, e.g., by determining the amount of cleaved versus the amount of uncleaved protein. In one embodiment, the amount of protein cleavage may be calculated by determining the ratio of the amount of cleaved protein in the growth medium to the amount of non-cleaved fusion protein in the growth medium per volume of cell culture.

A fusion polypeptide containing a KEX2 site pre-sequence or an optimized KEX2 site pre-sequence may, in certain embodiments, result in a fusion polypeptide that is cleaved to at least 30%, 40%, 50%, 60%, 70%, 80%, 90%, 95%, 97%, 98%, 99% or 100% efficiency, wherein 100% efficiency is a completely cleaved desired protein.

In other embodiments, the efficiency of secretion of a subject fusion polypeptide may be calculated by determining the amount of the secreted portion of that fusion polypeptide in the growth medium of a cell secreting that protein. This determination may be quantitative, qualitative, relative or absolute. In one embodiment, the amount of secreted protein in the growth medium of a cell secreting a subject fusion may be at least 10%, at least 30%, at least 50%, at least 70%, at least 90%, at least twice, at least five times, or at least ten times greater than the amount of the secreted protein secreted by a cell producing an equivalent fusion polypeptide that does not contain an optimized KEX2 pre-sequence.

In some embodiments the increase in secretion and/or cleavage may be measured against a standard KEX2 region defined as $GGGB_1B_2$, wherein $B_1B_2$ is KK, KR, RK or RR and preferably KR. In an embodiment, the amount of secreted protein or desired protein in the growth medium of a cell secreting a subject fusion may be at least 10%, at least 30%, at least 50%, at least 70%, at least 80%, at least 90%, at least 100%, at least 2×, at least 3×, at least 5×, and at least 10× greater than the amount of the secreted protein or desired protein secreted by an equivalent fusion polypeptide in an equivalent host under essentially the same conditions.

Screening Methods—

Screening methods for identifying optimized KEX2 site pre-sequences are also provided. These methods may include: a) altering a KEX2 site pre-sequence of a parental fusion polypeptide to produce a test polypeptide and b) evaluating secretion of the test fusion polypeptide by a filamentous fungal cell. In certain embodiments, the secretion and/or cleavage of the desired protein from test fusion polypeptides is compared to the secretion and/or cleavage of the parental fusion protein. In particular embodiments, the method includes evaluating the amount of a secreted protein of the fusion polypeptide in a growth medium relative to the amount of a secreted portion of the fusion polypeptide in a cell, per volume of culture, or assessing the amount of a secreted protein of a recombinant fusion polypeptide in a growth medium. In another embodiments the method includes evaluating the amount of a secreted protein (desired protein) released or cleaved from a fusion polypeptide in a growth medium relative to the amount of the secreted protein that remains in the form of the fusion polypetide (e.g. attached to the carrier protein).

In these screening assays, the parental fusion protein has an amino acid sequence that is schematically illustrated in FIG. 1, where X is any amino acid. In certain embodiments, the parental fusion protein and the test fusion protein may be identical except for their KEX2 site pre-sequences. A parental recombinant fusion protein and a test recombinant fusion protein may differ in one, two, three or four amino acids in the KEX-2 site pre-sequence. An alteration may be an amino acid substitution, insertion or deletion, and if there are two or three alterations, the alterations may be in contiguous amino acids, non-contiguous amino acids, or a combination of contiguous and non-contiguous amino acids.

In one embodiment, the KEX2 site pre-sequence of a parental fusion polypeptide may be altered to produce a plurality of different test fusion polypeptides that each contains different KEX2 site pre-sequences, and then evaluating secretion and/or cleavage of the test fusion polypeptides and the parental fusion polypeptides by a filamentous fungal cell.

These methods may be performed using protocols that are generally known (see, e.g., Ward et al (1990) Bio/Technology 8:435-440 and Spencer (1998) Eur. J. Biochem 258: 107-112, among others), in which a vector is introduced into a cell, the cell is cultured, and the cell culture is assayed for the presence of the cellular protein. In one embodiment, a recombinant nucleic acid encoding a parent fusion (the structure of which is shown in FIG. 1) is altered to produce a nucleic acid encoding a test polypeptide, and the two nucleic acids are used to transform identical filamentous fugal cells (which may be any of the host cells listed above). The two cell lines are cultured under identical conditions, and the efficiency of secretion and/or cleavage of the secreted portion of the protein is evaluated. The signal sequence, secreted protein, the KEX2 site and the KEX2 site pre-sequence of the parental fusion protein may be any known signal sequence, secreted protein, KEX2 site or KEX2 site pre-sequence, including those listed above.

As noted above, the efficiency of protein secretion or cleavage may be evaluated in many different ways, for example, by comparing the absolute or normalized amounts of secreted portion in growth media between the different cultures, or by comparing the amount of the secreted portion of the protein to the amount of the unsecreted portion of the protein. This evaluation may be quantitative, qualitative, relative or absolute, for example.

An optimized KEX2 site pre-sequence may be identified by testing a plurality of different test fusion proteins according to the above methods; and determining which of the different test fusion proteins is secreted and/or cleaved most efficiently; wherein the optimized KEX2 site pre-sequence is the KEX2 site pre-sequence of the test recombinant fusion protein that is secreted most efficiently.

A culture of cells that contains at least 10%, at least 20%, at least 30%, at least 50%, at least 70% and at least 95% more secreted or more desired protein than a control culture indicates that KEX2 site pre-sequence increases protein secretion and/or cleavage from those cells.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade (° C.), pressure is at or near atmospheric and the following abbreviations apply, M (Molar); μM (micromolar); N (Normal); mol (moles); mmol (millimoles); μmol (micromoles); nmol (nanomoles); g (grams); mg (milligrams) kg (kilograms); μg (micrograms); L (liters); ml (milliliters); h (hours); min (minutes); PAGE (polyacrylamide gel electrophoresis); kDa (kilodaltons); and by (base pairs). The following assays and methods are used in the examples provided below:

A. Construction of the pTrex4 Vector:

Synthetic DNA was cloned into a *Trichoderma* expression vector (pTrex4) to generate appropriate expression plasmids for use in the examples described below.

PTrex4 is a modified version of pTrex2 and derived from a pTrex3g expression vector. The construction of pTrex3g is described in detail in Example 6 of WO 05/001036. In brief, the pTrex3g is based on the *E. coli* vector pSL1180 (Pharmacia, Inc., Piscataway, N.J.) which is a pUC118 plasmid based vector with an extended multiple cloning site containing 64 hexamer restriction enzyme recognition sequences. It was designed as a Gateway destination vector (Hartley, J. L. et al., (2000) Genome Research 10:1788-1795) to allow insertion using Gateway Technology (Invitrogen) of any desired open reading frame between the promoter and terminator regions of the *T. reesei* cbh1 gene.

The details of pTrex4-her2 light chain DNA2.0 are as follows (FIG. 2 and FIG. 3): The plasmid is 10885 kb in size (SEQ ID NO: 103). Inserted into the polylinker region of pSL1180 are the following segments of DNA:

A 2.2 bp segment of DNA from the promoter region of the *T. reesei* cbh1;

DNA sequence of *T. reesei* cbh1 signal sequence (underlined); catalytic domain; linker (italics) (1570 bases) (SEQ ID NO: 104)

```
ATGTATCGGAAGTTGGCCGTCATCTCGGCCTTCTTGGCCACAGCTCGTGCTCAGTCGGCCTG

CACTCTCCAATCGGAGACTCACCCGCCTCTGACATGGCAGAAATGCTCGTCTGGTGGCACTT

GCACTCAACAGACAGGCTCCGTGGTCATCGACGCCAACTGGCGCTGGACTCACGCTACGAA

CAGCAGCACGAACTGCTACGATGGCAACACTTGGAGCTCGACCCTATGTCCTGACAACGAG

ACCTGCGCGAAGAACTGCTGTCTGGACGGTGCCGCCTACGCGTCCACGTACGGAGTTACCA

CGAGCGGTAACAGCCTCTCCATTGGCTTTGTCACCCAGTCTGCGCAGAAGAACGTTGGCGCT

CGCCTTTACCTTATGGCGAGCGACACGACCTACCAGGAATTCACCCTGCTTGGCAACGAGTT

CTCTTTCGATGTTGATGTTTCGCAGCTGCCGTAAGTGACTTACCATGAACCCCTGACGTATCT

TCTTGTGGGCTCCCAGCTGACTGGCCAATTTAAGGTGCGGCTTGAACGGAGCTCTCTACTTC

GTGTCCATGGACGCGGATGGTGGCGTGAGCAAGTATCCCACCAACACCGCTGGCGCCAAGT

ACGGCACGGGGTACTGTGACAGCCAGTGTCCCCGCGATCTGAAGTTCATCAATGGCCAGGC

CAACGTTGAGGGCTGGGAGCCGTCATCCAACAACGCAAACACGGGCATTGGAGGACACGG

AAGCTGCTGCTCTGAGATGGATATCTGGGAGGCCAACTCCATCTCCGAGGCTCTTACCCCCC

ACCCTTGCACGACTGTCGGCCAGGAGATCTGCGAGGGTGATGGGTGCGGCGGAACTTACTC

CGATAACAGATATGGCGGCACTTGCGATCCCGATGGCTGCGACTGGAACCCATACCGCCTG

GGCAACACCAGCTTCTACGGCCCTGGCTCAAGCTTTACCCTCGATACCACCAAGAAATTGAC

CGTTGTCACCCAGTTCGAGACGTCGGGTGCCATCAACCGATACTATGTCCAGAATGGCGTCA

CTTTCCAGCAGCCCAACGCCGAGCTTGGTAGTTACTCTGGCAACGAGCTCAACGATGATTAC

TGCACAGCTGAGGAGGCAGAATTCGGCGGATCCTCTTTCTCAGACAAGGGCGGCCTGACTC

AGTTCAAGAAGGCTACCTCTGGCGGCATGGTTCTGGTCATGAGTCTGTGGGATGATGTGAGT

TTGATGGACAAACATGCGCGTTGACAAAGAGTCAAGCAGCTGACTGAGATGTTACAGTACT

ACGCCAACATGCTGTGGCTGGACTCCACCTACCCGACAAACGAGACCTCCTCCACACCCGGT

GCCGTGCGCGGAAGCTGCTCCACCAGCTCCGGTGTCCCTGCTCAGGTCGAATCTCAGTCTCC

CAACGCCAAGGTCACCTTCTCCAACATCAAGTTCGGACCCATTGGCAGCACCGGCAACCCTA

GCGGCGGCAACCCTCCCGGCGGAAACCCGCCTGGCACCACCACCACCCGCCGCCCAGCCACTA

CCACTGGAAGCTCTCCCGGACCTACTAGT
```

The amino acid sequence of the *T. reesei* cbh1 signal sequence; catalytic domain; linker (480 amino acids) is represented below (SEQ ID NO: 105)

MYRKLAVISAFLATARAQSACTLQSETHPPLTWQKCSSGGTCTQQTGSVVIDANWRWT

HATNSSTNCYDGNTWSSTLCPDNETCAKNCCLDGAAYASTYGVTTSGNSLSIGFVTQSAQKNV

GARLYLMASDTTYQEFTLLGNEFSFDVDVSQLPCGLNGALYFVSMDADGGVSKYPTNTAGAKY

GTGYCDSQCPRDLKFINGQANVEGWEPSSNNANTGIGGHGSCCSEMDIWEANSISEALTPHPCTT

VGQEICEGDGCGGTYSDNRYGGTCDPDGCDWNPYRLGNTSFYGPGSSFTLDTTKKLTVVTQFE

TSGAINRYYVQNGVTFQQPNAELGSYSGNELNDDYCTAEEAEFGGSSFSDKGGLTQFKKATSGG

MVLVMSLWDDYYANMLWLDSTYPTNETSSTPGAVRGSCSTSSGVPAQVESQSPNAKVTFSNIK

FGPIGSTGN*PSGGNPPGGNPPGTTTTRRPATTTGSSPGPTS*

The plasmid also contains a cbh1 terminator, an *A. nidulans* amdS selectable marker and nucleotides encoding the antibody light chain.

B. Biolistic Transformation of *T. Reesei:*

In all examples below transformation was performed on a derivative of the quad deleted (Δchb1, Δcbh2, Δegl1, and Δegl2) *T. reesei* strain (WO 05/001036) originally derived from RL-P37 (Sheir-Neiss et al., (1984) Appl. Microbiol. Biotechnol. 20:46-53; U.S. Pat. No. 4,797,361) with the appropriate pTrex4 vector using the protocol outlined below.

A suspension of spores (approximately 5×10⁸ spores/ml) from the *Trichoderma* strain was prepared. 100 ul-200 ul of spore suspension was spread onto the center of plates of MM acetamide medium. MM acetamide medium had the following composition: 0.6 g/L acetamide; 1.68 g/L CsCl; 20 g/L glucose; 20 g/L $KH_2PO_4$; 0.6 g/L $CaCl_2.2H_2O$; 1 ml/L 1000× trace elements solution; 20 g/L Noble agar; pH 5.5. 1000× trace elements solution contained 5.0 g/l $FeSO_4.7H_2O$, 1.6 g/l $MnSO_4.H_2O$, 1.4 g/l $ZnSO_4.7H_2O$ and 1.0 g/l $CoCl_2.6H_2O$. The spore suspension was allowed to dry on the surface of the MM acetamide medium.

Transformation of the *Trichoderma* strain by the biolistic transformation method was accomplished using a Biolistic® PDS-1000/He Particle Delivery System from Bio-Rad (Hercules, Calif.) following the manufacturers instructions (see, WO 05/001036 and US 2006/0003408).

C. Transformation of *Aspergillus*—

The *Aspergillus* transformation protocol was a modification of the Campbell method (Campbell et at. (1989). Curr. Genet. 16:53-56). Also details of the transformation method for *Aspergillus niger* are disclosed in WO 03089614 and US Pat. Pub. 20050153399. Transformants were assayed for protein production on SDS gel and Western blot to select the transformants based on the amount of protein produced.

D. Fermentation of *T. Reesei* and *Aspergillus Niger* Strains Transformed with the Expression Vector:

In general the fermentation protocol as described in Foreman et al., (2003) J. Biol. Chem. 278:31988-31997 was followed.

E. Proflo Media

Contains: 30 g/L α-lactose; 6.5 g/L $(NH_4)_2SO_4$; 2 g/L $KH_2PO_4$; 0.3 g/L $MgSO_4.7H_2O$; 0.2 g/L $CaCl_2$; 1 ml/L 1000× trace element salt solution; 2 ml/L 10% Tween 80; 22.25 g/L Proflo cottonseed flour (Traders Protein, Memphis, Tenn.); 0.72 g/L $CaCO_3$.

F. Defined Media

Contains: 5 g/L $(NH_4)_2SO_4$; 33 g/L PIPPS buffer; 9 g/L casamino acids; 4.5 g/L $KH_2PO_4$; 1 g/L $CaCl_2$; 1 g/L $MgSO_4.7H_2O$; 5 ml/L Mazu DF60-P antifoam (Mazur Chemicals, Gurnee, Ill.); 1 ml/L 1000× trace elements solution. After autoclaving 40 ml of 40% lactose was added.

G. 1000× Trace Elements Solution

Contains: 5.0 g/l $FeSO_4.7H_2O$, 1.6 g/l $MnSO_4.H_2O$, 1.4 g/l $ZnSO_4.7H_2O$ and 1.0 g/l $CoCl_2.6H_2O$ H. Protein Analysis was accomplished by standard SDS gel and Western blot analysis.

Example 1

Construction of a Trastuzumab (Light Chain Expression Strain Containing a KRGGG (SEQ ID NO: 2) KEX2 Cleavage Site DNA (SEQ ID NO:1) encoding the light chain of trastuzumab according to the published amino acid sequence of antibody 4D5-8 (Carter et al, Proc. Natl. Acad. Sci. 1992 89: 4285-4289) was synthesized by DNA2.0 Inc. (1455 Adams Drive, Menlo Park, Calif. 94025).

(SEQ ID NO: 1)
ACTAGTAAACGCGGTGGCGGTGATATTCAAATGACACAATCTCCTTCTTCTCTGTCA

GCCTCAGTGGGCGACCGTGTGACGATTACTTGCCGCGCCTCTCAGGACGTTAACACT

GCCGTCGCATGGTACCAGCAGAAGCCAGGCAAGGCGCCCAAGCTTCTGATTTACAG

CGCTTCGTTCCTGTACTCTGGCGTGCCATCCCGCTTCTCTGGCAGCCGAAGCGGCAC

GGATTTCACCCTGACCATTTCGTCCCTGCAGCCCGAGGATTTCGCCACGTATTACTG

CCAGCAGCACTACACCACTCCACCCACCTTTGGCCAAGGAACGAGAGTCGAAATCA

CTCGCACGGTCGCTGCCCCTTCAGTCTTCATCTTCCCCCCCAGCGACGAACAGCTGA

AGTCTGGTACGGCCAGCGTCGTTTGCTTGCTTAATAACTTCTATCCGCGAGAGGCGA

AGGTCCAATGGAAGGTTGATAACGTTCTGCAGTCCGGCAATTCGCAGGAGAGCGTG

ACCGAGCAGGATTCAAAGGATAGCACCTACTCACTCAGCAGCACCCTGACGTTGTC

CAAGGCCGATTACGAGAAGCATAAGTTGTATGCATGCGAGGTCACCCACCAGGGAC

TGTCAAGCCCAGTTACCAAGTCGTTCAATCGAGGCGAGTGCTAAGGCGCGCC.

Figure 2:
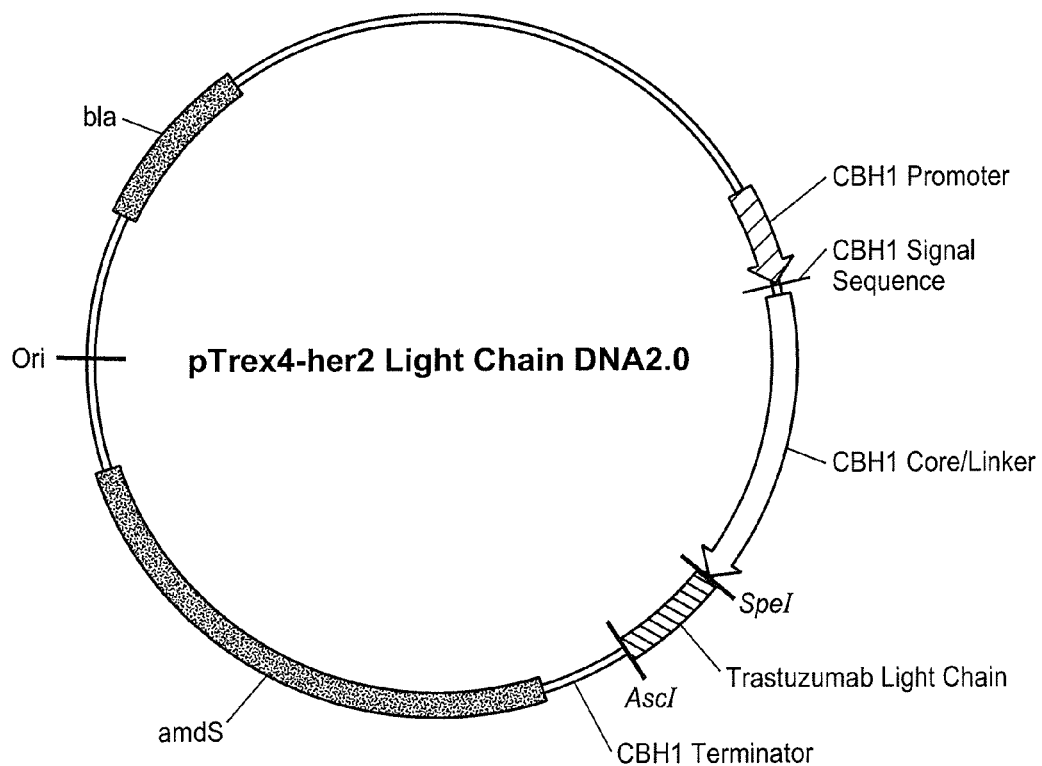
FIG. 2 depicts a map of the pTrex4-her2 light chain DNA2.0 plasmid used for the expression of a fusion polypeptide. The plasmid includes a *Trichoderma reesei* cbh1 promoter; a polynucleotide encoding a CBH1 signal sequence and carrier protein; a KEX2 region inserted immediately after the SpeI site, a polynucleotide encoding the desired protein illustrated as an antibody (trastuzumab) light chain; a *Trichoderma reesei* cellobiohydrolase (cbh1) terminator; an amdS *Aspergillus nidulans* acetamidase marker.

The light chain encoded by the DNA contains a KRGGG (SEQ ID NO:2) KEX2 cleavage site at its N-terminal end. The restriction sites SpeI and AscI were included for cloning proposes. The synthetic DNA was cloned into *Trichoderma* expression vector (pTrex4) to generate an expression plasmid named pTrex4-her2 light chain DNA2.0 (FIG. 2). The resultant plasmid encodes a fusion protein containing a *Trichoderma* CBHI core/linker region and the antibody light chain, separated by a KEX2 site. The plasmid was digested with XbaI restriction enzyme and transformed biolistically into a *Trichoderma reesei* strain derived from the quad deleted strain described in WO 05001036, example 5). More than 20 transformants were obtained and transferred to new plates. Twenty stable transformants were selected to grow in Proflo media for 2 days at 30° C. 5 mls of 2 days old culture from Proflo were transferred to 50 mls of Define media. The cultures were grown for 5 days at 28° C. Culture broths were centrifuged and supernatants were used for protein analysis. Western blot data (FIG. 4) indicated that more than 90% of the fusion protein was cleaved in the best light chain producing strain (transformant 1010-18, KRGGG variant). However, GGG will remain at the N-terminus of the cleaved antibody light chain which is undesirable. A band of about 50 kd was also detected in Western blot, which may result from dimerization of two light chain molecules.

Example 2

Construction of a Trastuzumab Light Chain Expression Strain Containing the GGGKR (SEQ ID NO: 5) KEX2 Cleavage Site Two primers (GGACTAGTGGTGGCGGTAAACGC-GATATTCAAATGACACAATCT C; SEQ ID NO:3 and AAGGCGCGCCTTAGCACTCGCCTCGATTG; SEQ ID NO:4) were synthesized by Invitrogen (1600 Faraday Avenue. Carlsbad, Calif. 92008) and used to amplify trastuzumab light chain DNA.

Figure 4:
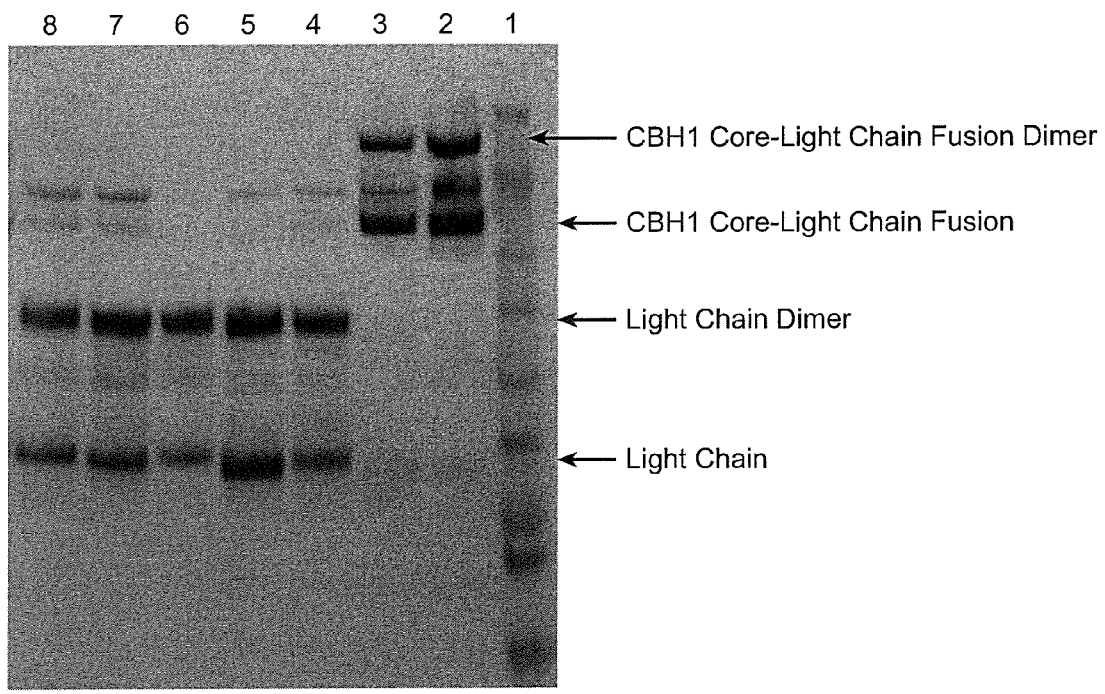
FIG. 4 shows a Western blot of supernatants of cultured *Trichoderma reesei* cells comprising KEX2 region sequences as further described in examples 1, 2, 3 and 4. Lane 1 represents a molecular weight marker (See Blue Plus 2, Invitrogen). Lanes 2 and 3 represent a GGGKR variant (SEQ ID NO: 5); lane 4 represents a GGGKRGGG variant (SEQ ID NO: 7); lane 5 represents a VAVEKR variant (SEQ ID NO: 9) KEX2 region encompassed by the invention; and lanes 6 and 7 represent a KRGGG variant (SEQ ID NO: 2).

The resulting PCR fragment encodes the antibody light chain containing a GGGKR (SEQ ID NO:5) sequence kex2 site at its N-terminal end. The PCR fragment was digested with restriction enzymes SpeI and AscI and cloned to expression Vector pTrex4 to generate a plasmid named as pTrex4-GGGKR-her2 DNA2.0. Fidelity of the PCR fragment was analyzed by DNA sequencing. The plasmid was digested with XbaI restriction enzyme and transformed biolistically using standard techniques into the *T. reesei* strain described above. More than 20 transformants were obtained and transferred to new plates. A total of 21 stable transformants were selected to grow in Proflo media for 2 days at 30° C. 5 mls of 2 days old culture from Proflo were transferred to 50 mls of Define media. The cultures were grown for 5 days at 28° C. Culture broths were centrifuged and supernatants were used. Western blot indicated that, more than 95% of the protein from transformant 1010-B5 (GGGKR variant) and transformant 1010-B6 (GGGKR variant), was an uncleaved fusion protein (FIG. 4). A band of about 150 kd was also detected in Western blot. It may result from dimerization of two CBHI core-light chain fusion molecules.

Example 3

Construction of a Trastuzumab Light Chain Expression Strain Containing a GGGKRGGG (SEQ ID NO: 7) KEX2 Cleavage Site Two oligos, GGACTAGTGGCGGTGGCAAACGCGGTG-GCGGTGATATTC (SEQ ID NO: 6) and AAGGCGCGCCT-TAGCACTCGCCTCGATTG (SEQ ID NO. 4), were synthesized by Invitrogen and used to amplify light chain DNA. The resulting PCR fragment encodes light chain and GGGKRGGG (SEQ ID NO:7) sequence for kex2 cleavage. The PCR fragment was digested with restriction enzymes SpeI and AscI and cloned to expression Vector pTrex4 to generate a plasmid named as pTrex4-GGGKRGGG-her2 light chain DNA2.0. Fidelity of the PCR fragment was analyzed by DNA sequencing. The plasmid was digested with XbaI restriction enzyme and transformed biolistically into the *T. reesei* strain as described above. More than 10 transformants were obtained and transferred to new plates. 3 stable transformants were selected to grow in Proflo media for 2 days at 30° C. 5 mls of 2 days old culture from Proflo were transferred to 50 mls of Define media. The cultures were grown for 5 days at 28° C. Culture broths were centrifuged and supernatants were used for protein analysis. Western gel data indicated that, in transformant 1011-1 (GGGKRGGG variant), more than 90% of the fusion protein was cleaved (FIG. 4). However, GGG remained at the N-terminus of the cleaved antibody light chain which is undesirable.

Example 4

Construction of a Trastuzumab Light Chain Expression Strain Containing a VAVEKR (SEQ ID NO: 9) KEX2 Region A VAVEKR (SEQ ID NO: 9) KEX2 region is found naturally in the proregion of the *T. reesei* high pI xylanase, Xyn2 (Torronen et al., (1992) Biotechnol. 10:1461-1465). To construct a fusion polypeptide according to the invention, two oligos, GGACTAGTGTCGCCGTTGAGAAACGC-GATATTCAAATGACACAAT CTCC (SEQ ID NO. 8) and AAGGCGCGCCTTAGCACTCGCCTCGATTG (SEQ ID NO. 4), were synthesized by Invitrogen and used to amplify light chain DNA.

The resulting PCR fragment encodes light chain and VAVEKR (SEQ ID NO:9) sequence for kex2 cleavage. The PCR fragment was digested with restriction enzymes SpeI and AscI and cloned to expression Vector pTrex4 to generate a plasmid named as pTrex4-VAVE-her2 light chain DNA2.0. Fidelity of the PCR fragment was analyzed by DNA sequencing. The plasmid was digested with XbaI restriction enzyme and transformed biolistically into the *T. reesei* strain as described above. More than 20 transformants were obtained and transferred to new plates. 6 stable transformants were selected to grow in Proflo media for 2 days at 30° C. 5 mls of 2 days old culture from Proflo were transferred to 50 mls of Define media. The cultures were grown for 5 days at 28° C. Culture broths were centrifuged and supernatants were used for protein analysis. Western gel data indicated that, in transformant 1012-2 (VAVEKR variant, SEQ ID NO: 9), more than 95% of the fusion proteins were cleaved (FIG. 4).

Example 5

Construction of a Trastuzumab Light Chain Expression Strain Containing Variants of the VAVEKR (SEQ ID NO: 9) KEX2 Region DNA (SEQ ID NO: 10) encoding the trastuzumab antibody light chain was synthesized by Geneart (Josef-Engert-Strasse 11, 93053 Regesburg, Germany).

```
                                                    (SEQ ID NO: 10)
ACTAGTAAGCGCGGCGGCGGCGAGGTCCAGCTCGTCGAGAGCGGCGGCGGCCTCGT

CCAGCCCGGCGGCAGCCTCCGCCTCAGCTGCGCCGCCAGCGGCTTCAACATCAAGG

ACACCTACATCCACTGGGTCCGCCAGGCCCCCGGCAAGGGCCTCGAGTGGGTCGCC

CGCATCTACCCCACCAACGGCTACACCCGCTACGCCGACAGCGTCAAGGGCCGCTT

CACCATCAGCGCCGACACCAGCAAGAACACCGCCTACCTCCAGATGAACAGCCTCC

GCGCCGAGGACACCGCCGTCTACTACTGCAGCCGCTGGGGCGGCGACGGCTTCTAC

GCCATGGACTACTGGGGCCAGGGCACCCTCGTCACGGTCTCCAGCGCCAGCACCAA

GGGCCCAAGCGTCTTTCCCCTCGCCCCCAGCAGCAAGAGCACCAGCGGCGGCACCG

CCGCCCTCGGCTGCCTCGTCAAGGACTACTTCCCCGAGCCCGTCACTGTCAGCTGGA

ACAGCGGCGCTCTCACCAGCGGCGTCCACACCTTCCCCGCCGTCCTCCAGAGCAGC

GGCCTCTACAGCCTCAGCAGCGTCGTCACCGTCCCCAGCAGCAGCCTCGGCACCCA

GACCTACATCTGCAACGTCAACCACAAGCCCAGCAACACCAAGGTCGACAAGCGCG

TCGAGCCCAAGAGCTGCGACAAGACCCACACCTGCCCCCCCTGCCCCGCCCCCGAG

CTGCTCGGCGGCCCCTCCGTCTTTCTCTTCCCCCCCAAGCCCAAGGACACCCTCATG

ATCAGCCGCACCCCCGAGGTCACCTGCGTCGTCGTCGATGTCAGCCACGAGGACCC

CGAGGTCAAGTTCAACTGGTACGTCGACGGCGTCGAGGTCCACAACGCCAAGACCA

AGCCCCGCGAGGAGCAGTACAACAGCACCTACCGCGTCGTCAGCGTCCTGACCGTC

CTCCACCAGGACTGGCTCAACGGCAAGGAGTACAAGTGCAAGGTCTCCAACAAGGC

CCTCCCCGCCCCCATCGAAAAGACCATCAG

CAAGGCCAAGGGCCAGCCCCGCGAGCCCCAGGTCTACACCCTCCCCCCCAGCCGCG

AGGAGATGACCAAGAACCAGGTCTCCCTCACCTGCCTGGTCAAGGGCTTCTACCCC

AGCGACATCGCCGTCGAGTGGGAGAGCAACGGCCAGCCCGAGAACAACTACAAGA

CCACCCCCCCCGTCCTCGACAGCGACGGCAGCTTCTTCCTCTACAGCAAGCTCACCG

TCGACAAGAGCCGCTGGCAGCAGGGCAACGTCTTTAGCTGCAGCGTCATGCACGAG

GCCCTCCACAACCACTACACCCAGAAGAGCCTCAGCCTCAGCCCCGGCAAGTAAGG

CGCG
```

Figure 5:
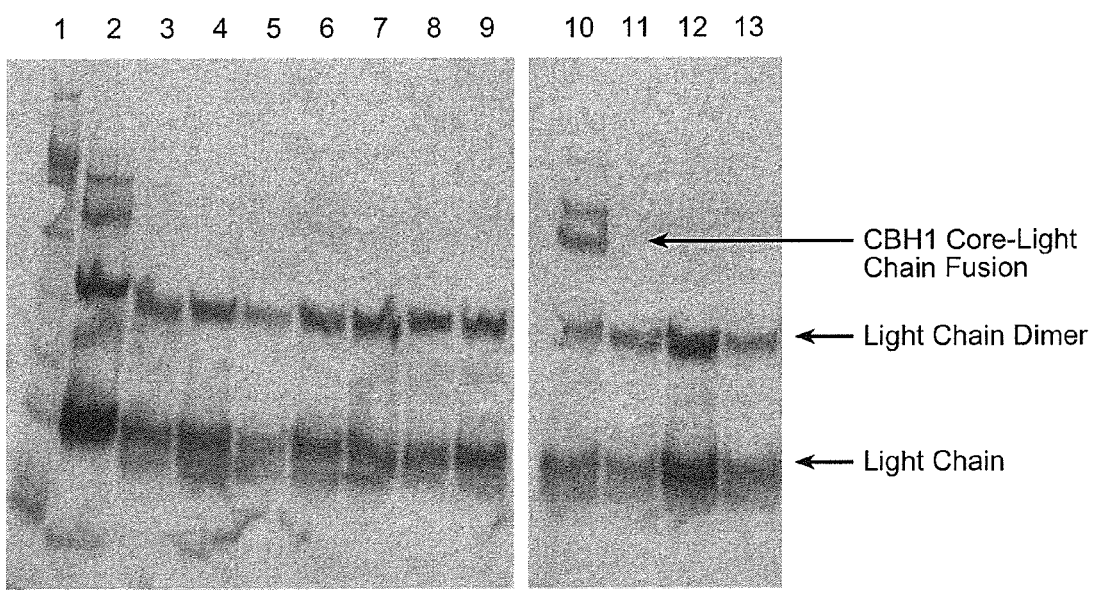
FIG. 5 shows a Western blot of supernatants of cultured *Trichoderma reesei* cells comprising KEX2 regions encompassed by the invention as further described in example 5. Lane 1 represents a molecular weight marker as described above. Lanes 2, 3, 4, 5, 6, 7, 8, 9, 10, 11, 12 and 13 correspondingly represent VAVEKR (SEQ ID NO: 9), VAVWKR (SEQ ID NO: 25), VAVGKR (SEQ ID NO: 26), VAVRKR (SEQ ID NO: 27), VAVTKR (SEQ ID NO: 28), VAVVKR (SEQ ID NO: 29), VAVAKR (SEQ ID NO: 30), VAVLKR (SEQ ID NO: 31), VAVDKR (SEQ ID NO: 32), VAVNKR (SEQ ID NO: 33), VAVYKR (SEQ ID NO: 34), VAVHKR (SEQ ID NO: 35) KEX2 regions.

This DNA encodes KRGGG (SEQ ID NO: 2) and the human antibody light chain. Two restriction sites SpeI and AscI were included for cloning proposes. The nucleotide sequence was mutated to remove an internal kex2 site by site-direct mutagenesis (Stratagene, 11011 North Torrey Pines Road, La Jolla, Calif. 92037) and two primers used for the mutagenesis in the PCR reaction are TCGAGATCAC-CCGCACCGTCGCG
GCGCCAAG (SEQ ID NO: 11) and CGACGGTGCGGGTGATCTCGACCTTGGTGCCCTGG CCG (SEQ ID NO: 12). The resulting light chain encoding DNA contained two substituted nucleotides at the DNA sequence which changed amino acid K to T.
Two oligos, GGACTAGTGTCGCCGTTGAGAAACGC-GACATCCAGATGACCCAGAGC (SEQ ID NO: 13) and CTAAAGGGAACAAAAGCTGGAGC (SEQ ID NO: 14), were synthesized by Invitrogen and used to amplify light chain DNA. The resulting PCR fragment encodes light chain and VAVEKR (SEQ ID NO: 9). The PCR fragment was digested with restriction enzymes SpeI and AscI and cloned to expression Vector pTrex4 to generate a plasmid named as pTrex4-VAVE-her2 light chain Geneart (KR-TR). Fidelity of the PCR fragment was analyzed by DNA sequencing. The plasmid was digested with XbaI restriction enzyme and co-transformed biolistically into the *T. reesei* strain with heavy chain expression plasmid. More than 40 transformants were obtained and transferred to new plates. More than 20 stable transformants were selected to grow in Proflo media for 2 days at 30° C. 5 mls of 2 days old culture from Proflo were transferred to 50 mls of Define media. The cultures were grown for 4 days at 28° C. Culture broths were centrifuged and supernatants were used for protein analysis. Western blot data indicated that in the VAVEKR variant (transformant 17-43), more than 90% of the fusion protein was cleaved (FIG. 5).

To generate amino acid changes at the glutamine residue of the KEX2 site pre-sequence of VAVEKR (SEQ ID NO: 9), a degenerate primer (GGACTAGTGTCGCCGTT-NNSAAACGCGACATCC AGATGACCCAGAG (SEQ ID NO:15) was synthesized and used in a PCR reaction with reverse primer (SEQ ID NO:14) to amplify DNA to generate a pool of PCR fragments. The mixed PCR fragments were cloned into *Trichoderma* expression vector (pTrex4). 13 clones were sequenced and 7 variants were produced (table 1). All 7 plasmids were transformed biolistically into the *T. reesei* strain. More than 40 transformants were obtained for each variant and transferred to new plates. For the first set of three variants (VAVWKR (SEQ ID NO: 25), VAVGKR (SEQ ID NO: 26) and VAVRKR (SEQ ID NO: 27)), 15 stable transformants for each variant were selected. For the second set of four variants (VAVTKR (SEQ ID NO: 28), VAVVKR (SEQ ID NO: 29), VAVAKR (SEQ ID NO: 30) and VAVLKR (SEQ ID NO: 31)), 11 stable transformants for each variant were selected. The selected transformants were grown in Proflo media for 2 days at 28° C. 5 mls of 2 days old culture from Proflo were transferred to 50 mls of Define media. The cultures were grown for 4 days at 28° C. Culture broths were centrifuged and supernatants were used for protein analysis.

A new primer (GGACTAGTGTCGCCGTTNA-CAAACGCGACATCCAGATGAC CCAGAG SEQ ID NO: 16) was synthesized and used in a PCR reaction with reverse primer (SEQ ID NO: 14) to amplify DNA to generate PCR fragments with multiple sequences. The mixed PCR fragments were cloned into *Trichoderma* expression vector (pTrex4). 10 clones were sequenced and 4 more variants (VAVDKR (SEQ ID NO: 32), VAVNKR (SEQ ID NO: 33), VAVYKR (SEQ ID NO: 34) and VAVHKR (SEQ ID NO: 35)) were produced. The plasmids were transformed biolistically into the *Trichoderma* strain described above. More than 40 transformants for each variant were obtained and transferred to new plates. 10 stable transformants for each variant were selected and grown in Proflo media for 2 days at 28° C. 5 mls of 2 days old culture from Proflo were transferred to 50 mls of Define media. The cultures were grown for 4 days at 28° C. Culture broths were centrifuged and supernatants were used for protein analysis.

One transformant (the best light chain producing transformant) from each variant at the glutamine residue was selected to be compared. Western analysis indicated that the variant VAVYKR (SEQ ID NO: 34) produced more light chain than any other variant. VAVTKR (SEQ ID NO: 28) and VAVDKR (SEQ ID NO: 32) variants had more fusion protein indicating less efficient cleavage. (FIG. 5).

To generate amino acid changes at the first Valine residue of the KEX2 pre-sequence site (VAVEKR, SEQ ID NO: 9), a degenerate primer (GGACTAGTNNSGCCGTC-GAGAAGCGCGACATCCAGATGACCCAG AG; SEQ ID NO:17) was synthesized which was used in a PCR reaction with reverse primer CTAAAGGGAACAAAAGCTGGAGC (SEQ ID NO:14) to amplify DNA to generate PCR fragment with multiple sequences. The mixed PCR fragments were cloned into *Trichoderma* expression vector (pTrex4). 30 clones were sequenced and 13 variants (MAVEKR (SEQ ID NO: 36), GAVEKR (SEQ ID NO: 37), AAVEKR (SEQ ID NO:38), LAVEKR (SEQ ID NO: 39), WAVEKR (SEQ ID NO: 40), KAVEKR (SEQ ID NO: 41), PAVEKR (SEQ ID NO: 42), RAVEKR (SEQ ID NO: 43), NAVEKR (SEQ ID NO: 44), TAVEKR (SEQ ID NO: 45), SAVEKR (SEQ ID NO: 46), QAVEKR (SEQ ID NO: 47) and EAVEKR (SEQ ID NO: 48)) were produced A new primer was designed, synthesized (GGACTAGTNWCGCCGTCGAGAAGCGCGA-CATCCAGATGACCCAGAG SEQ ID NO:18) and used in a PCR reaction with reverse primer CTAAAGGGAA-CAAAAGCTGGAGC (SEQ ID NO:14) to amplify DNA to generate PCR fragment with multiple sequences. The mixed PCR fragments were cloned into *Trichoderma* expression vector (pTrex4). 19 clones were sequenced and 5 more variants (YAVEKR (SEQ ID NO: 49), FAVEKR (SEQ ID NO: 50), DAVEKR (SEQ ID NO: 51), HAVEKR (SEQ ID NO: 52) and IAVEKR (SEQ ID NO: 53)) were produced. The plasmids containing the following 11 variants (MAVEKR (SEQ ID NO: 36), GAVEKR (SEQ ID NO: 37), AAVEKR (SEQ ID NO: 38), LAVEKR (SEQ ID NO:39), WAVEKR (SEQ ID NO: 40), KAVEKR (SEQ ID NO: 41), PAVEKR (SEQ ID NO: 42), HAVEKR (SEQ ID NO: 52), DAVEKR (SEQ ID NO: 51), SAVEKR (SEQ ID NO: 46) and QAVEKR (SEQ ID NO: 47)) were transformed biolistically into the *T. reesei* strain.

More than 20 transformants were obtained for each variant and transferred to new plates. More than 8 stable transformants for each variant were selected and grown in Proflo media for 2 days at 28° C. 5 mls of 2 days old culture from Proflo were transferred to 50 mls of Define media. The cultures were grown for 4 days at 28° C. Culture broths were centrifuged and supernatants were analyzed by protein SDS-PAGE. One transformant (the best producing transformant) from each variant was selected. Western analysis indicated (FIG. 6) that all variants produced light chain. All showed less than 95% cleavage except LAVEKR (SEQ ID NO: 39). This variant showed more efficient KEX2 cleavage than the VAVEKR (SEQ ID NO: 9) variant.

Figure 7:
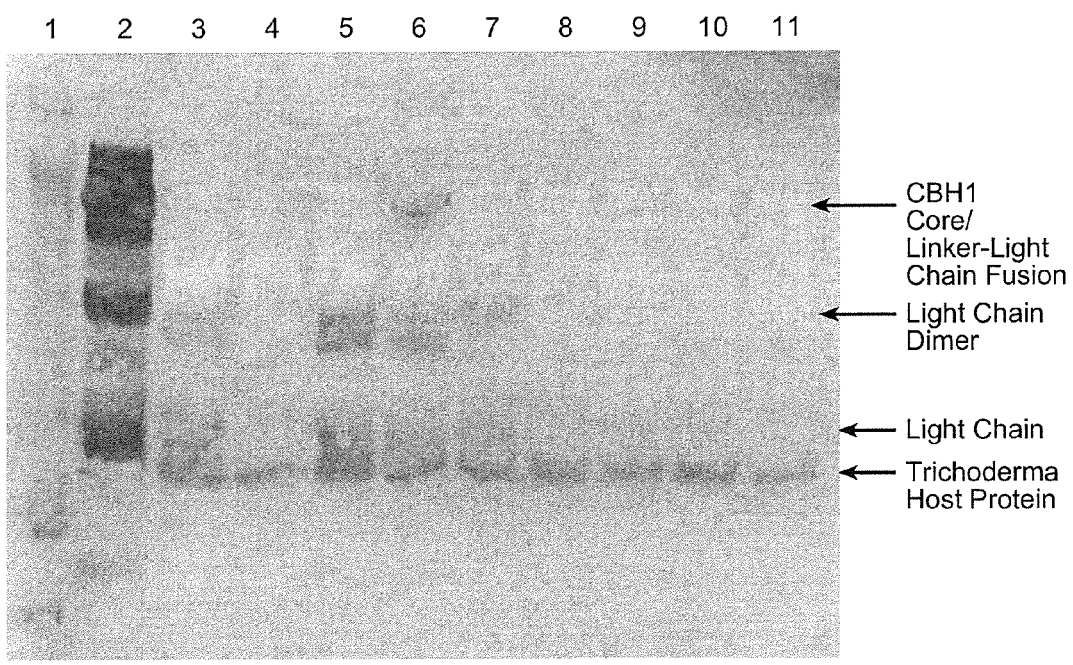
FIG. 7 shows a Western blot of supernatants of cultured *Trichoderma reesei* cells containing KEX2 region sequences as further described in example 5. Lane 1 represents a molecular weight marker, as described above. Lanes 2, 3, 4, 5, 6, 7, 8, 9, 10 and 11 correspondingly represent VAVEKR (SEQ ID NO: 9), VGVEKR (SEQ ID NO: 56), VTVEKR (SEQ ID NO: 65), VEVEKR (SEQ ID NO: 55), VPVEKR (SEQ ID NO: 62), VWVEKR (SEQ ID NO: 67), VKVEKR (SEQ ID NO: 58), VRVEKR (SEQ ID NO: 63), VVVEKR (SEQ ID NO: 66), and VIVEKR (SEQ ID NO: 57) KEX2 regions.

To generate amino acid changes at the Alanine residue of the KEX2 region (VAVEKR, (SEQ ID NO: 9)), a degenerate primer (GGACTAGTGTCNNSGTTGAGAAAGGCGA- CATCCAGATGACCCA GAGC; SEQ ID NO:19) was synthesized which was used in a PCR reaction with reverse primer (SEQ ID NO:14) to amplify DNA to generate PCR fragment with multiple sequences. The mixed PCR fragments were cloned into *Trichoderma* expression vector (pTrex4). 96 clones were sequenced and 15 variants (VDVEKR (SEQ ID NO: 54), VEVEKR (SEQ ID NO: 55), VGVEKR (SEQ ID NO: 56), VIVEKR (SEQ ID NO: 57), VKVEKR (SEQ ID NO: 58), VLVEKR (SEQ ID NO: 59), VMVEKR (SEQ ID NO: 60), VNVEKR (SEQ ID NO: 61), VPVEKR (SEQ ID NO:62), VRVEKR (SEQ ID NO: 63), VSVEKR (SEQ ID NO: 64), VTVEKR (SEQ ID NO: 65), VVVEKR (SEQ ID NO: 66), VWVEKR (SEQ ID NO: 67) and VYVEKR (SEQ ID NO: 68)) were produced. 5 plasmids were transformed biolistically into the *T. reesei* strain. More than 20 transformants for each variant were obtained and transferred to new plates. For this first set of 5 variants (VGVEKR (SEQ ID NO: 56), VTVEKR (SEQ ID NO: 65), VWVEKR (SEQ ID NO: 67), VEVEKR (SEQ ID NO: 55) and VPVEKR (SEQ ID NO: 62)), 10 stable transformants were selected. For the second set of 4 variants (VKVEKR (SEQ ID NO: 58), VRVEKR (SEQ ID NO: 63), VVVEKR (SEQ ID NO: 66) and VIVEKR (SEQ ID NO: 57)), 10 stable transformants were selected. The selected transformants were grown in Proflo media for 2 days at 28° C. 5 mls of 2 days old culture from Proflo were transferred to 50 mls of Define media. The cultures were grown for 4 days at 28° C. Culture broths were centrifuged and supernatants are analyzed by protein SDS gel. One transformant (the best producing transformant) from each variant was selected to be compared (table 1). Western analysis (FIG. 7) indicated that only the free light chain could be detected in the three variants: VGVEKR (SEQ ID NO: 56); VEVEKR (SEQ ID NO: 55) and VWVEKR (SEQ ID NO: 67). The variant VPVEKR (SEQ ID NO: 62) produced less free light chain and some uncleaved CBHI-light fusion.

Figure 8:
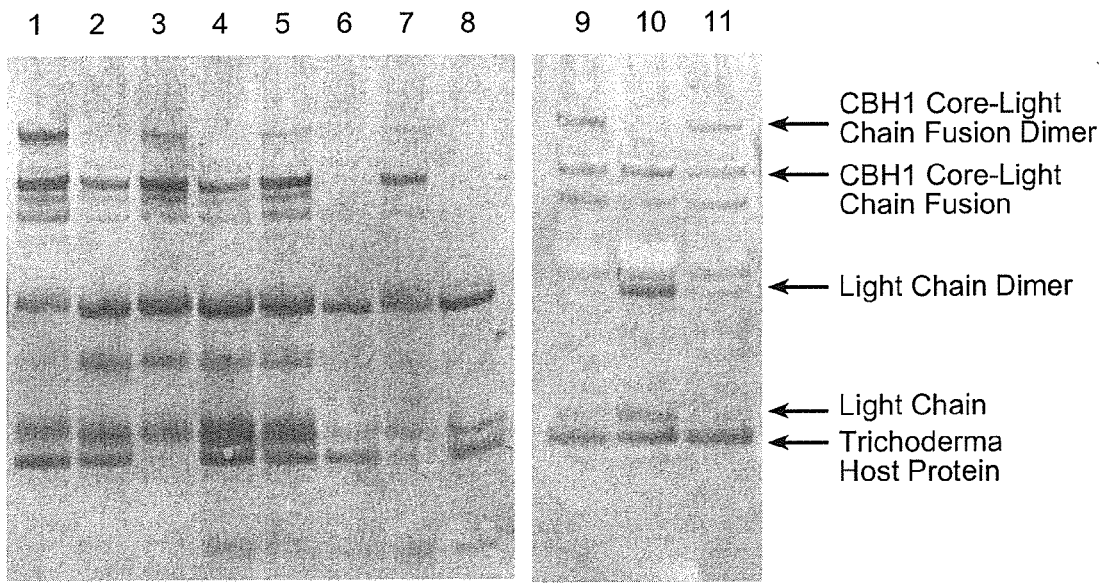
FIG. 8 shows a Western blot of supernatants of cultured *Trichoderma reesei* cells containing KEX2 region sequences as further described in example 5. Lanes 1-11 correspondingly represent VADEKR (SEQ ID NO: 70), VAAEKR (SEQ ID NO: 69), VAFEKR (SEQ ID NO: 72), VAGEKR (SEQ ID NO: 73), VAIEKR (SEQ ID NO: 74), VANEKR (SEQ ID NO: 76), VALEKR (SEQ ID NO: 75), VASEKR (SEQ ID NO: 79), VAREKR (SEQ ID NO: 78) and VAPEKR (SEQ ID NO: 83) KEX2 regions.

To generate amino acid changes at the second valine residue of the KEX2 site (VAVEKR, SEQ ID NO: 9), a degenerate primer (GGACTAGTGTCGCCNNSGAGAAACGCGA-CATCCAGATGACCCAG AG; SEQ ID NO:20) was synthesized which was used in a PCR reaction with reverse primer (SEQ ID NO:14) to amplify DNA to generate PCR fragment with multiple sequences. The mixed PCR fragments were cloned into *Trichoderma* expression vector (pTrex4). 36 clones were sequenced and 15 variants (VAAEKR (SEQ ID NO: 69), VADEKR (SEQ ID NO: 70), VAEEKR (SEQ ID NO: 71), VAFEKR (SEQ ID NO: 72), VAGEKR (SEQ ID NO: 73), VAIEKR (SEQ ID NO: 74), VALEKR (SEQ ID NO: 75), VANEKR (SEQ ID NO: 76), VAQEKR (SEQ ID NO: 77), VAREKR (SEQ ID NO: 78), VASEKR (SEQ ID NO: 79), VATEKR (SEQ ID NO: 80), VAWEKR (SEQ ID NO: 81), VAYEKR (SEQ ID NO: 82) and VAPEKR (SEQ ID NO: 83)) were produced. Plasmids were transformed biolistically into the *T. reesei* strain. More than 20 transformants for each variant were obtained and transferred to new plates. For the first set of 8 variants (VAAEKR (SEQ ID NO: 69), VADEKR (SEQ ID NO: 70), VAEEKR (SEQ ID NO: 71), VAFEKR (SEQ ID NO: 72), VAGEKR (SEQ ID NO: 73), VANEKR (SEQ ID NO: 76), VALEKR (SEQ ID NO: 75) and VAIEKR (SEQ ID NO: 74)), 10 stable transformants were selected. For the second set of 2 variants (VASEKR (SEQ ID NO: 79) and VAREKR (SEQ ID NO: 78), 8 stable transformants were selected. Only 4 transformants were selected for VAPEKR (SEQ ID NO: 83) variant. The selected transformants were grown in Proflo media for 2 days at 28° C. 5 mls of 2 days old culture from Proflo were transferred to 50 mls of Define media. The cultures were grown for 4 days at 28° C. Culture broths were centrifuged and supernatants were analyzed. One transformant (the best producing transformant) from each variant was selected to be compared (Table 1). Western analysis (FIG. 8) indicated that VAIEKR (SEQ ID NO: 74) and VALEKR (SEQ ID NO: 75) generated complete cleavage of the fusion polypeptide since a fusion band was not observed in the gel. Western blot (FIG. 8) indicated that VAFEKR (SEQ ID NO: 72) produced the highest amount of antibody light chain even though the cleavage was not 100%.

TABLE 1

| | | | |
|---|---|---|---|
| MAVEKR (SEQ ID NO: 36) | VKVEKR (SEQ ID NO: 58) | VAAEKR (SEQ ID NO: 69) | VAVWKR (SEQ ID NO: 25) |
| GAVEKR (SEQ ID NO: 37) | VRVEKR (SEQ ID NO: 63) | VADEKR (SEQ ID NO: 70) | VAVGKR (SEQ ID NO:26) |
| AAVEKR (SEQ ID NO: 38) | VVVEKR (SEQ ID NO: 66) | VAEEKR (SEQ ID NO: 71) | VAVRKR (SEQ ID NO:27) |
| LAVEKR (SEQ ID NO: 39) | VIVEKR (SEQ ID NO: 57) | VAFEKR (SEQ ID NO: 72) | VAVTKR (SEQ ID NO:28) |
| WAVEKR (SEQ ID NO: 40) | VEVE (SEQ ID NO: 55) | VAGEKR (SEQ ID NO: 73) | VAVVKR (SEQ ID NO: 29) |
| KAVEKR (SEQ ID NO: 41) | VGVEKR (SEQ ID NO: 56) | VAIEKR (SEQ ID NO: 74) | VAVAKR (SEQ ID NO: 30) |
| PAVEKR (SEQ ID NO: 42) | VPVEKR (SEQ ID NO: 62) | VALEKR (SEQ ID NO: 75) | VAVLKR (SEQ ID NO: 31) |
| SAVEKR (SEQ ID NO: 46) | VTVEKR (SEQ ID NO: 65) | VANEKR (SEQ ID NO: 76) | VAVDKR (SEQ ID NO: 32) |
| QAVEKR (SEQ DI NO: 47) | VWVEKR (SEQ ID NO: 67) | VASEKR (SEQ ID NO: 79) | VAVNKR (SEQ ID NO: 33) |
| DAVEKR (SEQ ID NO: 51) | | VAREKR (SEQ ID NO: 78) | VAVYKR (SEQ ID NO: 34) |

TABLE 1-continued

| HAVEKR | VAPEKR | VAVHKR |
|---|---|---|
| (SEQ ID NO: 52) | (SEQ ID NO: 83) | (SEQ ID NO: 35) |

Example 6

Figure 6:
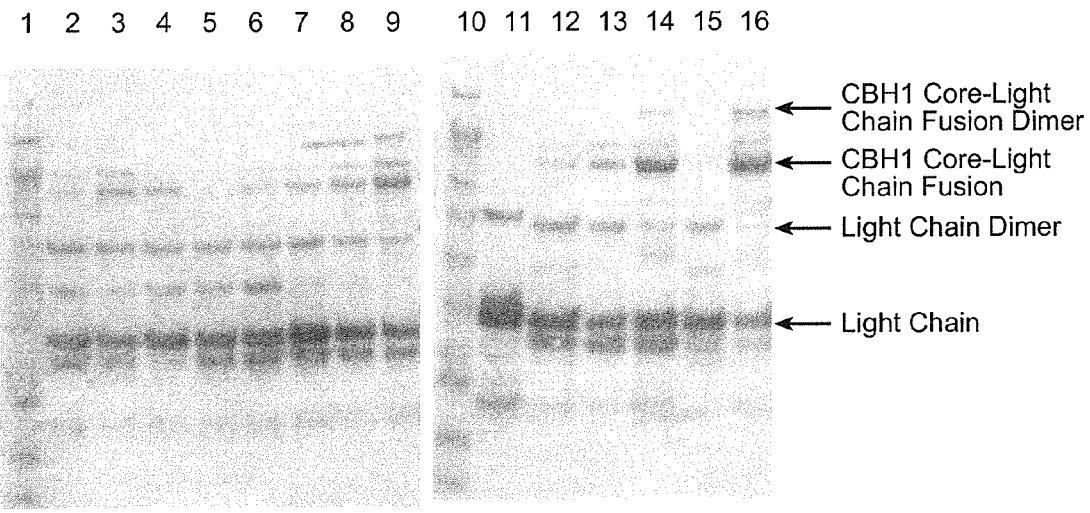
FIG. 6 shows a Western blot of supernatants of cultured *Trichoderma reesei* cells containing KEX2 region sequences as further described in examples 5, 6, and 7. Lanes 1 and 10 represent a molecular weight marker, as described above. Lanes 2, 3, 4, 5, 6, 7, 8, 9, 11, 12, 13, 14, 15 and 16 correspondingly represent AAVEKR (SEQ ID NO: 38), GAVEKR (SEQ ID NO: 37), MAVEKR (SEQ ID NO: 36), LAVEKR (SEQ ID NO: 39), WAVEKR (SEQ ID NO: 40), KAVEKR (SEQ ID NO: 41), PAVEKR (SEQ ID NO: 42), DAVEKR (SEQ ID NO: 51), VAVEKR (SEQ ID NO: 9), HAVEKR (SEQ ID NO: 52), QAVEKR (SEQ ID NO: 47), SAVEKR (SEQ ID NO: 46), NVISKR (SEQ ID NO: 22), and SDVTKR (SEQ ID NO: 24) KEX2 regions.

Construction of a Trastuzumab Light Chain Expression Strain Containing the NVISKR (SEQ ID NO: 22) KEX2 Region A NVISKR KEX2 region is found naturally in the prosequence of the *A. niger* glucoamylase (glaA). To construct a fusion polypeptide an oligo, GGACTAGTAACGTCATCAG-CAAGCGCGACATCCAGATGACCCAGAGC (SEQ ID NO. 21) was synthesized by Invitrogen and used to amplify light chain DNA with reverse primer (SEQ ID NO. 14), The resulting PCR fragment encodes light chain and NVISKR (SEQ ID NO:22) sequence for kex2 cleavage. The PCR fragment was digested with restriction enzymes SpeI and AscI and cloned to expression Vector pTrex4 to generate a plasmid named as pTrex4-NVIS-her2 light chain geneart (KR-TR). Fidelity of the PCR fragment was analyzed by DNA sequencing. The plasmid was transformed biolistically into the *Trichoderma reesei* strain. More than 20 transformants were obtained and transferred to new plates. 10 stable transformants were selected to grow in Proflo media for 2 days at 30° C. 5 mls of 2 days old culture from Proflo were transferred to 50 mls of Define media. The cultures were grown for 5 days at 28° C. Culture broths were centrifuged and supernatants were used for protein analysis. Western analysis indicated that more than 95% of the fusion proteins were cleaved (FIG. 6).

Example 7

Construction of a Trastuzumab Light Chain Expression Strain Containing the SDVTKR (SEQ ID NO: 24) KEX2 Region An oligo, GGACTAGTAGCGACGTCACCAAGCGC-GACATCCAGATGACCCAGAGC (SEQ ID NO: 23) was synthesized by Invitrogen and used to amplify light chain DNA with reverse primer (SEQ ID NO: 14), The resulting PCR fragment encodes light chain and SDVTKR (SEQ ID NO: 24) sequence for kex2 cleavage. The PCR fragment was digested with restriction enzymes SpeI and AscI and cloned to expression Vector pTrex4 to generate a plasmid named as pTrex4-SDVT-her2 light chain geneart (KR-TR). Fidelity of the PCR fragment was analyzed by DNA sequencing. The plasmid was transformed biolistically into the *Trichoderma reesei* strain. More than 20 transformants were obtained and transferred to new plates. 10 stable transformants were selected to grow in Proflo media for 2 days at 30° C. 5 mls of 2 days old culture from Proflo were transferred to 50 mls of Define media. The cultures were grown for 5 days at 28° C. Culture broths were centrifuged and supernatants were used for protein analysis. Western analysis indicated that more than 50% of the fusion proteins were cleaved (FIG. 6).

Example 8

Construction of a Trastuzumab Light Chain Expression Strain Containing the VAVEKR (SEQ ID NO: 9) KEX2 Region in *Aspergillus Niger*

The plasmid (pTrex4-VAVE-her2 light chain geneart (KR-TR) from Example 5 was digested with SpeI and AscI. The end of the DNA fragment of the AscI cutting site was blunted by T4 DNA polymerase. The fragment was isolated on a 1.2% agarose gel and ligated to *A. niger* expression plasmid (pSL-GAMpR2-BBI as disclosed in US Patent Publication No. 2005 0153399) which was cut with NheI and BstEII with the BstEII end blunted with T4 DNA polymerase. The new plasmid, named pSLGAMpR2-VAVE-her2 LC geneart was transformed into *A. niger* strain dgr246:Δamy5;pyr—which is derived from the dgr246:ΔGAP:pyr—strain disclosed in US Pat. Pub. 20050153399. The difference being that the protein level of α-amylase is greatly reduced in this plasmid because of a mutation.

The dgr246ΔGAP:pyr2- is derived from strain dgr246 P2 which has the pepA gene deleted, is pyrG minus and has undergone several rounds of mutagenesis and screening or selection for improved production of a heterologous gene product (Ward, M. et al., 1993, Appl. Microbiol. Biotech. 39:738-743 and references therein). To create strain dgr246ΔGAP:pyr2- the glaA (glucoamylase) gene was deleted in strain dgr246 P2 using exactly the same deletion plasmid (pΔGAM NB-Pyr) and procedure as reported by Fowler, T. et al (1990) Curr. Genet. 18:537-545. Briefly, the deletion was achieved by transformation with a linear DNA fragment having glaA flanking sequences at either end and with part of the promoter and coding region of the glaA gene replaced by the *Aspergillus nidulans* pyrG gene as selectable marker. Transformants in which the linear fragment containing the glaA flanking sequences and the pyrG gene had integrated at the chromosomal glaA locus were identified by Southern blot analysis. This change had occurred in transformed strain dgr246ΔGAP. Spores from this transformant were plated onto medium containing fluoroorotic acid and spontaneous resistant mutants were obtained as described by van Hartingsveldt, W. et al. (1987) Mol. Gen. Genet. 206:71-75. One of these, dgr246ΔGAP:pyr2-, was shown to be a uridine auxotroph strain which could be complemented by transformation with plasmids bearing a wild-type pyrG gene.

Figure 9:
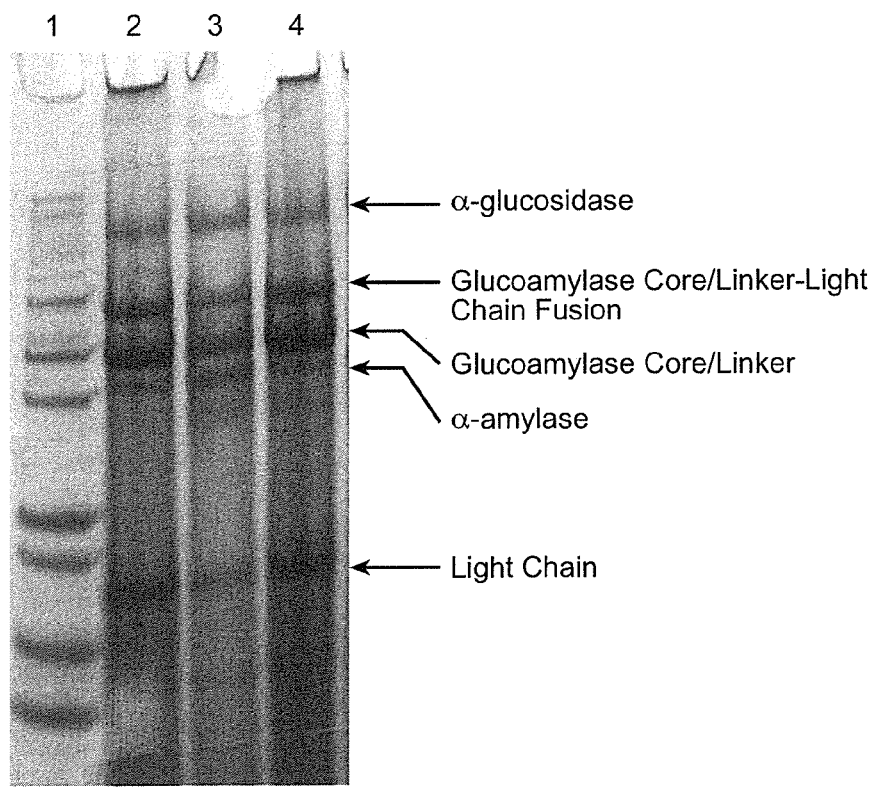
FIG. 9 shows an SDS-PAGE gel of supernatants of cultured *A. niger* cells containing a VAVEKR (SEQ ID NO: 9) KEX2 region as further described in example 8. Lane 1 represents a molecular weight marker, Marker 12 MW standard (Invitrogen). Lanes 2, 3, and 4 represent 3 transformants and correspond respectively to transformants A 10, A 11 and A 12.

More than 20 transformants were obtained and transferred to new plates. 17 transformants were grown in Promosoy medium for 5 days at 28° C. Culture broths were centrifuged and supernatants were used for protein SDS PAGE and Western analysis. Data indicated that all transformants produced antibody light chain. The transformant #A12 produced the most antibody light chain, and 60-70% of the fusion protein was cleaved (FIG. 9).

The preceding description merely illustrates principles of exemplary embodiments. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

It is claimed:

1. A fusion DNA construct encoding a fusion polypeptide comprising in operable linkage from the 5' end of said construct,
a promoter,
a first DNA molecule, which is different from any one of the second, the third, and the fourth DNA molecules, encoding a signal sequence,
a second DNA molecule, which is different from any one of the first, the third, and the fourth DNA molecules, encoding a carrier protein,
a third DNA molecule, which is different from any one of the first, the second, and the fourth DNA molecules, encoding a KEX2 region, said region comprising a KEX2 site ($B_1B_2$) and a KEX2 site pre-sequence X4X3X2X1 immediately 5' to the KEX2 site, wherein X4 is V, S, N, L, or K, X3 is A, V, D, W, E, or P; X2 is V, I, L or F; and X1 is E, S, T or Y, wherein the pre-sequence is not NVIS (SEQ ID NO:85; and
a fourth DNA molecule, which is different from any one of the first, the second, and the third DNA molecules, encoding a protein.

2. The fusion DNA construct of claim 1, wherein the first DNA molecule and second DNA molecule encode a *Trichoderma* CBH1 signal sequence and carrier protein or a *Trichoderma* endoglucanase signal sequence and carrier protein.

3. The fusion DNA construct of claim 1, wherein the first DNA molecule and second DNA molecule encode a glucoamylase signal sequence and carrier protein or an alpha amylase signal sequence and carrier protein.

4. The fusion DNA construct of claim 1, wherein the desired protein is an enzyme.

5. The fusion DNA construct of claim 1, wherein the desired protein is a therapeutic protein.

6. The fusion DNA construct of claim 5, wherein the therapeutic protein is an antibody.

7. The fusion DNA construct of claim 6, wherein the antibody is a light chain or heavy chain monoclonal antibody.

8. The fusion DNA construct of claim 1, wherein the first DNA molecule and second DNA molecule encode a CBH I signal sequence and carrier protein and the fourth DNA molecule encodes an antibody light chain or fragment thereof.

9. The fusion DNA construct of claim 1, wherein the first DNA molecule and second DNA molecule encode a glucoamylase signal sequence and carrier protein and the fourth DNA molecule encodes an antibody light chain or fragment thereof.

10. A host cell comprising the fusion DNA construct of claim 1.

11. The host cell of claim 10, wherein said host cell is a *Trichoderma* host cell.

12. The host cell of claim 11, wherein the *Trichoderma* cell is a *T. reesei* cell.

13. A vector comprising the fusion DNA construct of claim 1.

14. A host cell comprising the vector of claim 13.

15. The host cell of claim 14, wherein the host cell is a *Trichoderma* host cell.

16. A process for producing a desired protein in a filamentous fungal cell comprising:
a) obtaining a filamentous fungal host cell comprising a fusion DNA construct according to claim 1;
b) culturing the host cell under suitable conditions which allow for the expression and production of the desired protein; and
c) recovering the desired protein.

17. The process according to claim 16, wherein the host cell is a *Trichoderma* strain.

18. The process according to claim 17, wherein the *Trichoderma* cell is a *T. reesei* host cell.

19. The process according to claim 16, wherein the desired protein is an immunoglobulin.

20. The process according to claim 19, wherein the immunoglobulin is a monoclonal antibody.

21. The process according to claim 20, wherein the monoclonal antibody is a light chain or heavy chain monoclonal antibody or fragment thereof.

22. The process according to claim 20, wherein the host cell is a *Trichoderma* cell, the desired protein is a light chain antibody and the KEX2 region of the third DNA molecule is a sequence selected from VAVWKR (SEQ ID NO: 25), VAVGKR (SEQ ID NO: 26), VAVTKR (SEQ ID NO: 28), VAVVKR (SEQ ID NO: 29), VAVDKR (SEQ ID NO: 32), WAVEKR (SEQ ID NO: 40), PAVEKR (SEQ ID NO: 42), QAVEKR (SEQ ID NO: 47), HAVEKR (SEQ ID NO: 52), and VASEKR (SEQ ID NO: 79).

23. The method according to claim 18, wherein the KEX2 region of the third DNA molecule is a sequence selected from VAVWKR (SEQ ID NO: 25), VAVGKR (SEQ ID NO: 26), VAVTKR (SEQ ID NO: 28), VAVVKR (SEQ ID NO: 29), VAVDKR (SEQ ID NO: 32), WAVEKR (SEQ ID NO: 40), PAVEKR (SEQ ID NO: 42), QAVEKR (SEQ ID NO: 47), HAVEKR (SEQ ID NO: 52), and VASEKR (SEQ ID NO: 79).

* * * * *

```
                        SEQUENCE LISTING

<160> NUMBER OF SEQ ID NOS: 111

<210> SEQ ID NO 1
<211> LENGTH: 674
<212> TYPE: DNA
<213> ORGANISM: Artificial Sequence
<220> FEATURE:
<223> OTHER INFORMATION: synthetic humanized monoclonal antibody

<400> SEQUENCE: 1
actagtaaac gcggtggcgg tgatattcaa atgacacaat ctccttcttc tctgtcagcc      60
tcagtgggcg accgtgtgac gattacttgc cgcgcctctc aggacgttaa cactgccgtc     120
gcatggtacc agcagaagcc aggcaaggcg cccaagcttc tgatttacag cgcttcgttc     180
ctgtactctg gcgtgccatc ccgcttctct ggcagccgaa gcggcacgga tttcaccctg     240
accatttcgt ccctgcagcc cgaggatttc gccacgtatt actgccagca gcactacacc     300
actccaccca cctttggcca aggaacgaga gtcgaaatca ctcgcacggt cgctgccct      360 tcagtcttca tcttcccccc cagcgacgaa cagctgaagt ctggtacggc cagcgtcgtt     420
tgcttgctta ataacttcta tccgcgagag gcgaaggtcc aatggaaggt tgataacgtt     480
ctgcagtccg gcaattcgca ggagagcgtg accgagcagg attcaaagga tagcacctac     540
tcactcagca gcaccctgac gttgtccaag gccgattacg agaagcataa gttgtatgca     600
tgcgaggtca cccaccaggg actgtcaagc ccagttacca agtcgttcaa tcgaggcgag     660
tgctaaggcg cgcc                                                      674

<210> SEQ ID NO 2
<211> LENGTH: 5
<212> TYPE: PRT
<213> ORGANISM: Artificial Sequence
<220> FEATURE:
<223> OTHER INFORMATION: synthetic KEX2 variant

<400> SEQUENCE: 2

Lys Arg Gly Gly Gly
1               5

<210> SEQ ID NO 3
<211> LENGTH: 44
<212> TYPE: DNA
<213> ORGANISM: Artificial Sequence
<220> FEATURE:
<223> OTHER INFORMATION: Synthetic primer

<400> SEQUENCE: 3
ggactagtgg tggcggtaaa cgcgatattc aaatgacaca atct                       44

<210> SEQ ID NO 4
<211> LENGTH: 29
<212> TYPE: DNA
<213> ORGANISM: Artificial Sequence
<220> FEATURE:
<223> OTHER INFORMATION: Synthetic primer

<400> SEQUENCE: 4
aaggcgcgcc ttagcactcg cctcgattg                                        29
```

```
<210> SEQ ID NO 5
<211> LENGTH: 5
<212> TYPE: PRT
<213> ORGANISM: Artificial Sequence
<220> FEATURE:
<223> OTHER INFORMATION: synthetic KEX2 variant

<400> SEQUENCE: 5

Gly Gly Gly Lys Arg
1               5

<210> SEQ ID NO 6
<211> LENGTH: 39
<212> TYPE: DNA
<213> ORGANISM: Artificial Sequence
<220> FEATURE:
<223> OTHER INFORMATION: Synthetic primer

<400> SEQUENCE: 6
ggactagtgg cggtggcaaa cgcggtggcg gtgatattc                    39

<210> SEQ ID NO 7
<211> LENGTH: 8
<212> TYPE: PRT
<213> ORGANISM: Artificial Sequence
<220> FEATURE:
<223> OTHER INFORMATION: synthetic KEX2 variant

<400> SEQUENCE: 7

Gly Gly Gly Lys Arg Gly Gly Gly
1               5

<210> SEQ ID NO 8
<211> LENGTH: 49
<212> TYPE: DNA
<213> ORGANISM: Artificial Sequence
<220> FEATURE:
<223> OTHER INFORMATION: Synthetic primer

<400> SEQUENCE: 8
ggactagtgt cgccgttgag aaacgcgata ttcaaatgac acaatctcc         49

<210> SEQ ID NO 9
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 9

Val Ala Val Glu Lys Arg
1               5

<210> SEQ ID NO 10
<211> LENGTH: 1380
<212> TYPE: DNA
<213> ORGANISM: Artificial Sequence
<220> FEATURE:
<223> OTHER INFORMATION: synthetic humanized monoclonal antibody

<400> SEQUENCE: 10
actagtaagc gcggcggcgg cgaggtccag ctcgtcgaga gcggcggcgg cctcgtccag    60
cccggcggca gcctccgcct cagctgcgcc gccagcggct tcaacatcaa ggacacctac   120
atccactggg tccgccaggc ccccggcaag ggctcgagt gggtcgcccg catctacccc    180
accaacggct acacccgcta cgccgacagc gtcaagggcc gcttcaccat cagcgccgac   240
```

```
accagcaaga acaccgccta cctccagatg aacagcctcc gcgccgagga caccgccgtc    300
tactactgca gccgctgggg cggcgacggc ttctacgcca tggactactg gggccagggc    360
accctcgtca cggtctccag cgccagcacc aagggcccaa gcgtctttcc cctcgccccc    420
agcagcaaga gcaccagcgg cggcaccgcc gccctcggct gcctcgtcaa ggactacttc    480
cccgagcccg tcactgtcag ctggaacagc ggcgctctca ccagcggcgt ccacaccttc    540
cccgccgtcc tccagagcag cggcctctac agcctcagca gcgtcgtcac cgtccccagc    600
agcagcctcg gcacccagac ctacatctgc aacgtcaacc acaagcccag caacaccaag    660
gtcgacaagc gcgtcgagcc caagagctgc gacaagaccc acacctgccc ccctgcccc     720 gcccccgagc tgctcggcgg ccctccgtc tttctcttcc ccccaagcc caaggacacc      780 ctcatgatca gccgcacccc cgaggtcacc tgcgtcgtcg tcgatgtcag ccacgaggac    840
cccgaggtca agttcaactg gtacgtcgac ggcgtcgagg tccacaacgc caagaccaag    900
ccccgcgagg agcagtacaa cagcacctac cgcgtcgtca gcgtcctgac cgtcctccac    960
caggactggc tcaacggcaa ggagtacaag tgcaaggtct ccaacaaggc cctccccgcc    1020
cccatcgaaa agaccatcag caaggccaag ggccagcccc gcgagcccca ggtctacacc    1080 ctcccccca gccgcgagga gatgaccaag aaccaggtct ccctcacctg cctggtcaag     1140
ggcttctacc ccagcgacat cgccgtcgag tgggagagca cggccagcc cgagaacaac     1200 tacaagacca cccccccgt cctcgacagc gacggcagct tcttcctcta cagcaagctc     1260
accgtcgaca gagccgctg gcagcagggc aacgtcttta gctgcagcgt catgcacgag     1320
gccctccaca accactacac ccagaagagc ctcagcctca gccccggcaa gtaaggcgcg    1380
```

```
<210> SEQ ID NO 11
<211> LENGTH: 31
<212> TYPE: DNA
<213> ORGANISM: Artificial Sequence
<220> FEATURE:
<223> OTHER INFORMATION: Synthetic primer

<400> SEQUENCE: 11
tcgagatcac ccgcaccgtc gcggcgccaa g                                     31

<210> SEQ ID NO 12
<211> LENGTH: 38
<212> TYPE: DNA
<213> ORGANISM: Artificial Sequence
<220> FEATURE:
<223> OTHER INFORMATION: Synthetic primer

<400> SEQUENCE: 12
cgacggtgcg ggtgatctcg accttggtgc cctggccg                              38

<210> SEQ ID NO 13
<211> LENGTH: 47
<212> TYPE: DNA
<213> ORGANISM: Artificial Sequence
<220> FEATURE:
<223> OTHER INFORMATION: Synthetic primer

<400> SEQUENCE: 13
ggactagtgt cgccgttgag aaacgcgaca tccagatgac ccagagc                    47

<210> SEQ ID NO 14
<211> LENGTH: 23
<212> TYPE: DNA
<213> ORGANISM: Artificial Sequence
```

```
<220> FEATURE:
<223> OTHER INFORMATION: Synthetic primer

<400> SEQUENCE: 14
ctaaagggaa caaaagctgg agc                                              23

<210> SEQ ID NO 15
<211> LENGTH: 46
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(19)
<223> OTHER INFORMATION: n is a, c, g, or t

<400> SEQUENCE: 15
ggactagtgt cgccgttnns aaacgcgaca tccagatgac ccagag                     46

<210> SEQ ID NO 16
<211> LENGTH: 46
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(18)
<223> OTHER INFORMATION: n is a, c, g, or t

<400> SEQUENCE: 16
ggactagtgt cgccgttnac aaacgcgaca tccagatgac ccagag                     46

<210> SEQ ID NO 17
<211> LENGTH: 46
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(10)
<223> OTHER INFORMATION: n is a, c, g, or t

<400> SEQUENCE: 17
ggactagtnn sgccgtcgag aagcgcgaca tccagatgac ccagag                     46

<210> SEQ ID NO 18
<211> LENGTH: 46
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or t

<400> SEQUENCE: 18
ggactagtnw cgccgtcgag aagcgcgaca tccagatgac ccagag                     46

<210> SEQ ID NO 19
<211> LENGTH: 47
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
```

```
<222> LOCATION: (12)..(13)
<223> OTHER INFORMATION: n is a, c, g, or t

<400> SEQUENCE: 19
ggactagtgt cnnsgttgag aaaggcgaca tccagatgac ccagagc          47

<210> SEQ ID NO 20
<211> LENGTH: 46
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(16)
<223> OTHER INFORMATION: n is a, c, g, or t

<400> SEQUENCE: 20
ggactagtgt cgccnnsgag aaacgcgaca tccagatgac ccagag           46

<210> SEQ ID NO 21
<211> LENGTH: 47
<212> TYPE: DNA
<213> ORGANISM: Artificial Sequence
<220> FEATURE:
<223> OTHER INFORMATION: Synthetic primer

<400> SEQUENCE: 21
ggactagtaa cgtcatcagc aagcgcgaca tccagatgac ccagagc          47

<210> SEQ ID NO 22
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 22

Asn Val Ile Ser Lys Arg
1               5

<210> SEQ ID NO 23
<211> LENGTH: 47
<212> TYPE: DNA
<213> ORGANISM: Artificial Sequence
<220> FEATURE:
<223> OTHER INFORMATION: Synthetic primer

<400> SEQUENCE: 23
ggactagtag cgacgtcacc aagcgcgaca tccagatgac ccagagc          47

<210> SEQ ID NO 24
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 24

Ser Asp Val Thr Lys Arg
1               5

<210> SEQ ID NO 25
<211> LENGTH: 6
<212> TYPE: PRT
<213> ORGANISM: Artificial Sequence
<220> FEATURE:
<223> OTHER INFORMATION: synthetic KEX2 variant
```

```
<400> SEQUENCE: 25

Val Ala Val Trp Lys Arg
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 26

Val Ala Val Gly Lys Arg
1               5

<210> SEQ ID NO 27
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 27

Val Ala Val Arg Lys Arg
1               5

<210> SEQ ID NO 28
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 28

Val Ala Val Thr Lys Arg
1               5

<210> SEQ ID NO 29
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 29

Val Ala Val Val Lys Arg
1               5

<210> SEQ ID NO 30
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 30

Val Ala Val Ala Lys Arg
1               5

<210> SEQ ID NO 31
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 31
```

```
Val Ala Val Leu Lys Arg
1               5

<210> SEQ ID NO 32
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 32

Val Ala Val Asp Lys Arg
1               5

<210> SEQ ID NO 33
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 33

Val Ala Val Asn Lys Arg
1               5

<210> SEQ ID NO 34
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 34

Val Ala Val Tyr Lys Arg
1               5

<210> SEQ ID NO 35
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 35

Val Ala Val His Lys Arg
1               5

<210> SEQ ID NO 36
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 36

Met Ala Val Glu Lys Arg
1               5

<210> SEQ ID NO 37
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 37

Gly Ala Val Glu Lys Arg
```

-continued

```
<210> SEQ ID NO 38
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 38

Ala Ala Val Glu Lys Arg
1               5

<210> SEQ ID NO 39
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 39

Leu Ala Val Glu Lys Arg
1               5

<210> SEQ ID NO 40
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 40

Trp Ala Val Glu Lys Arg
1               5

<210> SEQ ID NO 41
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 41

Lys Ala Val Glu Lys Arg
1               5

<210> SEQ ID NO 42
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 42

Pro Ala Val Glu Lys Arg
1               5

<210> SEQ ID NO 43
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 43

Arg Ala Val Glu Lys Arg
1               5
```

```
<210> SEQ ID NO 44
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 44

Asn Ala Val Glu Lys Arg
1               5

<210> SEQ ID NO 45
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 45

Thr Ala Val Glu Lys Arg
1               5

<210> SEQ ID NO 46
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 46

Ser Ala Val Glu Lys Arg
1               5

<210> SEQ ID NO 47
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 47

Gln Ala Val Glu Lys Arg
1               5

<210> SEQ ID NO 48
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 48

Glu Ala Val Glu Lys Arg
1               5

<210> SEQ ID NO 49
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 49

Tyr Ala Val Glu Lys Arg
1               5

<210> SEQ ID NO 50
```

```
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 50

Phe Ala Val Glu Lys Arg
1               5

<210> SEQ ID NO 51
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 51

Asp Ala Val Glu Lys Arg
1               5

<210> SEQ ID NO 52
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 52

His Ala Val Glu Lys Arg
1               5

<210> SEQ ID NO 53
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 53

Ile Ala Val Glu Lys Arg
1               5

<210> SEQ ID NO 54
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 54

Val Asp Val Glu Lys Arg
1               5

<210> SEQ ID NO 55
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 55

Val Glu Val Glu Lys Arg
1               5

<210> SEQ ID NO 56
<211> LENGTH: 6
<212> TYPE: PRT
```

```
<213> ORGANISM: Artificial Sequence
<220> FEATURE:
<223> OTHER INFORMATION: synthetic KEX2 variant

<400> SEQUENCE: 56

Val Gly Val Glu Lys Arg
1               5

<210> SEQ ID NO 57
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 57

Val Ile Val Glu Lys Arg
1               5

<210> SEQ ID NO 58
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 58

Val Lys Val Glu Lys Arg
1               5

<210> SEQ ID NO 59
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 59

Val Leu Val Glu Lys Arg
1               5

<210> SEQ ID NO 60
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 60

Val Met Val Glu Lys Arg
1               5

<210> SEQ ID NO 61
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 61

Val Asn Val Glu Lys Arg
1               5

<210> SEQ ID NO 62
<211> LENGTH: 6
<212> TYPE: PRT
<213> ORGANISM: Artificial Sequence
<220> FEATURE:
```

<223> OTHER INFORMATION: synthetic KEX2 variant

<400> SEQUENCE: 62

Val Pro Val Glu Lys Arg
1               5

<210> SEQ ID NO 63
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 63

Val Arg Val Glu Lys Arg
1               5

<210> SEQ ID NO 64
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 64

Val Ser Val Glu Lys Arg
1               5

<210> SEQ ID NO 65
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 65

Val Thr Val Glu Lys Arg
1               5

<210> SEQ ID NO 66
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 66

Val Val Val Glu Lys Arg
1               5

<210> SEQ ID NO 67
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 67

Val Trp Val Glu Lys Arg
1               5

<210> SEQ ID NO 68
<211> LENGTH: 6
<212> TYPE: PRT
<213> ORGANISM: Artificial Sequence
<220> FEATURE:
<223> OTHER INFORMATION: synthetic KEX2 variant

```
<400> SEQUENCE: 68

Val Tyr Val Glu Lys Arg
1               5

<210> SEQ ID NO 69
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 69

Val Ala Ala Glu Lys Arg
1               5

<210> SEQ ID NO 70
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 70

Val Ala Asp Glu Lys Arg
1               5

<210> SEQ ID NO 71
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 71

Val Ala Glu Glu Lys Arg
1               5

<210> SEQ ID NO 72
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 72

Val Ala Phe Glu Lys Arg
1               5

<210> SEQ ID NO 73
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 73

Val Ala Gly Glu Lys Arg
1               5

<210> SEQ ID NO 74
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 74
```

```
Val Ala Ile Glu Lys Arg
1               5

<210> SEQ ID NO 75
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 75

Val Ala Leu Glu Lys Arg
1               5

<210> SEQ ID NO 76
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 76

Val Ala Asn Glu Lys Arg
1               5

<210> SEQ ID NO 77
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 77

Val Ala Gln Glu Lys Arg
1               5

<210> SEQ ID NO 78
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 78

Val Ala Arg Glu Lys Arg
1               5

<210> SEQ ID NO 79
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 79

Val Ala Ser Glu Lys Arg
1               5

<210> SEQ ID NO 80
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 80

Val Ala Thr Glu Lys Arg
1               5
```

```
<210> SEQ ID NO 81
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 81

Val Ala Trp Glu Lys Arg
1               5

<210> SEQ ID NO 82
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 82

Val Ala Tyr Glu Lys Arg
1               5

<210> SEQ ID NO 83
<211> LENGTH: 6
<212> TYPE: PRT
<213> ORGANISM: Artificial Sequence
<220> FEATURE:
<223> OTHER INFORMATION: synthetic KEX2 variant

<400> SEQUENCE: 83

Val Ala Pro Glu Lys Arg
1               5

<210> SEQ ID NO 84
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 84

Val Ala Val Glu
1

<210> SEQ ID NO 85
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 85

Asn Val Ile Ser
1

<210> SEQ ID NO 86
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 86

Ser Asp Val Thr
1
```

```
<210> SEQ ID NO 87
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 87

Val Ala Val Tyr
1

<210> SEQ ID NO 88
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 88

Leu Ala Val Glu
1

<210> SEQ ID NO 89
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 89

Lys Ala Val Glu
1

<210> SEQ ID NO 90
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 90

Val Ala Ile Glu
1

<210> SEQ ID NO 91
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 91

Val Ala Leu Glu
1

<210> SEQ ID NO 92
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 92

Val Ala Phe Glu
1

<210> SEQ ID NO 93
<211> LENGTH: 4
```

```
<212> TYPE: PRT
<213> ORGANISM: Artificial Sequence
<220> FEATURE:
<223> OTHER INFORMATION: synthetic KEX2 site presequence

<400> SEQUENCE: 93

Val Trp Val Glu
1

<210> SEQ ID NO 94
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 94

Val Glu Val Glu
1

<210> SEQ ID NO 95
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 95

Val Pro Val Glu
1

<210> SEQ ID NO 96
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 96

Thr Ser Thr Tyr
1

<210> SEQ ID NO 97
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 97

Ala Ser Ile Ser
1

<210> SEQ ID NO 98
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 98

Ala Thr Ala Ser
1

<210> SEQ ID NO 99
<211> LENGTH: 4
<212> TYPE: PRT
<213> ORGANISM: Artificial Sequence
```

```
<220> FEATURE:
<223> OTHER INFORMATION: synthetic KEX2 site presequence

<400> SEQUENCE: 99

Thr Ala Ser Gln
1

<210> SEQ ID NO 100
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 100

Thr Ala Ser Leu
1

<210> SEQ ID NO 101
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 101

Ser Val Ile Ser
1

<210> SEQ ID NO 102
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 102

Thr Ser Arg Asp
1

<210> SEQ ID NO 103
<211> LENGTH: 10885
<212> TYPE: DNA
<213> ORGANISM: Artificial Sequence
<220> FEATURE:
<223> OTHER INFORMATION: synthetic pTrex4-her2 vector

<400> SEQUENCE: 103
aagcttaata cttctcgagc tctgtacatg tccggtcgcg acgtacgcgt atcgatggcg      60
ccagctgcag gcggccgcct gcagccactt gcagtcccgt ggaattctca cggtgaatgt     120 aggcctttg  tagggtagga attgtcactc aagcaccccc aacctccatt acgcctcccc     180
catagagttc ccaatcagtg agtcatggca ctgttctcaa atagattggg gagaagttga     240
cttccgccca gagctgaagg tcgcacaacc gcatgatata gggtcggcaa cggcaaaaaa     300
gcacgtggct caccgaaaag caagatgttt gcgatctaac atccaggaac ctggatacat     360
ccatcatcac gcacgaccac tttgatctgc tggtaaactc gtattcgccc taaaccgaag     420
tgacgtggta aatctacacg tgggccccctt tcggtatact gcgtgtgtct tctctaggtg    480
ccattctttt cccttcctct agtgttgaat tgtttgtgtt ggagtccgag ctgtaactac     540
ctctgaatct ctggagaatg gtggactaac gactaccgtg cacctgcatc atgtatataa     600
tagtgatcct gagaaggggg gtttggagca atgtgggact tgatggtca tcaaacaaag     660 aacgaagacg cctcttttgc aaagttttgt ttcggctacg gtgaagaact ggatacttgt     720
```

```
tgtgtcttct gtgtattttt gtggcaacaa gaggccagag acaatctatt caaacaccaa    780
gcttgctctt ttgagctaca agaacctgtg gggtatatat ctagagttgt gaagtcggta    840
atcccgctgt atagtaatac gagtcgcatc taaatactcc gaagctgctg cgaacccgga    900
gaatcgagat gtgctggaaa gcttctagcg agcggctaaa ttagcatgaa aggctatgag    960
aaattctgga gacggcttgt tgaatcatgg cgttccattc ttcgacaagc aaagcgttcc    1020
gtcgcagtag caggcactca ttcccgaaaa aactcggaga ttcctaagta gcgatggaac    1080
cggaataata taataggcaa tacattgagt tgcctgacg  gttgcaatgc aggggtactg    1140
agcttggaca taactgttcc gtaccccacc tcttctcaac ctttggcgtt tccctgattc    1200
agcgtacccg tacaagtcgt aatcactatt aacccagact gaccggacgt gttttgccct    1260
tcatttggag aaataatgtc attgcgatgt gtaatttgcc tgcttgaccg actgggctg    1320 ttcgaagccc gaatgtagga ttgttatccg aactctgctc gtagaggcat gttgtgaatc    1380
tgtgtcgggc aggacacgcc tcgaaggttc acggcaaggg aaaccaccga tagcagtgtc    1440
tagtagcaac ctgtaaagcc gcaatgcagc atcactggaa aatacaaacc aatggctaaa    1500
agtacataag ttaatgccta aagaagtcat ataccagcgg ctaataattg tacaatcaag    1560
tggctaaacg taccgtaatt tgccaacggc ttgtggggtt gcagaagcaa cggcaaagcc    1620
ccacttcccc acgtttgttt cttcactcag tccaatctca gctggtgatc ccccaattgg    1680
gtcgcttgtt tgttccggtg aagtgaaaga agacagaggt aagaatgtct gactcggagc    1740
gttttgcata caaccaaggg cagtgatgga agacagtgaa atgttgacat tcaaggagta    1800
tttagccagg gatgcttgag tgtatcgtgt aaggaggttt gtctgccgat acgacgaata    1860
ctgtatagtc acttctgatg aagtggtcca tattgaaatg taagtcggca ctgaacaggc    1920
aaaagattga gttgaaactg cctaagatct cgggccctcg ggccttcggc ctttgggtgt    1980
acatgtttgt gctccgggca aatgcaaagt gtggtaggat cgaacacact gctgcccttta   2040 ccaagcagct gagggtatgt gataggcaaa tgttcagggg ccactgcatg gtttcgaata    2100
gaaagagaag cttagccaag aacaatagcc gataaagata gcctcattaa acggaatgag    2160
ctagtaggca aagtcagcga atgtgtatat ataaaggttc gaggtccgtg cctccctcat    2220
gctctcccca tctactcatc aactcagatc ctccaggaga cttgtacacc atcttttgag    2280
gcacagaaac ccaatagtca accgcggact gcgcatcatg tatcggaagt tggccgtcat    2340
ctcggccttc ttggccacag ctcgtgctca gtcggcctgc actctccaat cggagactca    2400
cccgcctctg acatggcaga aatgctcgtc tggtggcact tgcactcaac agacaggctc    2460
cgtggtcatc gacgccaact ggcgctggac tcacgctacg aacagcagca cgaactgcta    2520
cgatggcaac acttggagct cgaccctatg tcctgacaac gagacctgcg cgaagaactg    2580
ctgtctggac ggtgccgcct acgcgtccac gtacggagtt accacgagcg gtaacagcct    2640
ctccattggc tttgtcaccc agtctgcgca gaagaacgtt ggcgctcgcc tttacctat    2700 ggcgagcgac acgacctacc aggaattcac cctgcttggc aacgagttct ctttcgatgt    2760
tgatgtttcg cagctgccgt aagtgactta ccatgaaccc ctgacgtatc ttcttgtggg    2820
ctcccagctg actggccaat ttaaggtgcg gcttgaacgg agctctctac ttcgtgtcca    2880
tggacgcgga tggtggcgtg agcaagtatc ccaccaacac cgctgcgcc  aagtacggca    2940 cggggtactg tgacagccag tgtccccgcg atctgaagtt catcaatggc caggccaacg    3000
ttgagggctg ggagccgtca tccaacaacg caaacacggg cattggagga cacggaagct    3060
gctgctctga gatggatatc tgggaggcca actccatctc cgaggctctt acccccacc    3120
```

```
cttgcacgac tgtcggccag gagatctgcg agggtgatgg gtgcggcgga acttactccg    3180
ataacagata tggcggcact tgcgatcccg atggctgcga ctggaaccca taccgcctgg    3240
gcaacaccag cttctacggc cctggctcaa gctttaccct cgataccacc aagaaattga    3300
ccgttgtcac ccagttcgag acgtcgggtg ccatcaaccg atactatgtc cagaatggcg    3360
tcactttcca gcagcccaac gccgagcttg tagttactc tggcaacgag ctcaacgatg    3420
attactgcac agctgaggag gcagaattcg gcggatcctc tttctcagac aagggcggcc    3480
tgactcagtt caagaaggct acctctggcg gcatggttct ggtcatgagt ctgtgggatg    3540
atgtgagttt gatggacaaa catgcgcgtt gacaaagagt caagcagctg actgagatgt    3600
tacagtacta cgccaacatg ctgtggctgg actccaccta cccgacaaac gagacctcct    3660
ccacacccgg tgccgtgcgc ggaagctgct ccaccagctc cggtgtccct gctcaggtcg    3720
aatctcagtc tcccaacgcc aaggtcacct tctccaacat caagttcgga cccattggca    3780
gcaccggcaa cctagcggc ggcaaccctc ccggcggaaa cccgcctggc accaccacca    3840
cccgccgccc agccactacc actggaagct ctcccggacc tactagtaaa cgcggtggcg    3900
gtgatattca aatgacacaa tctccttctt ctctgtcagc ctcagtgggc gaccgtgtga    3960
cgattacttg ccgcgcctct caggacgtta acactgccgt cgcatggtac cagcagaagc    4020
caggcaaggc gcccaagctt ctgatttaca gcgcttcgtt cctgtactct ggcgtgccat    4080
cccgcttctc tggcagccga agcggcacgg atttcaccct gaccatttcg tccctgcagc    4140
ccgaggattt cgccacgtat tactgccagc agcactacac cactccaccc acctttggcc    4200
aaggaacgag agtcgaaatc actcgcacgg tcgctgcccc ttcagtcttc atcttccccc    4260
ccagcgacga acagctgaag tctggtacgg ccagcgtcgt ttgcttgctt aataacttct    4320
atccgcgaga ggcgaaggtc caatggaagg ttgataacgt tctgcagtcc ggcaattcgc    4380
aggagagcgt gaccgagcag gattcaaagg atagcaccta ctcactcagc agcaccctga    4440
cgttgtccaa ggccgattac gagaagcata agttgtatgc atgcgaggtc acccaccagg    4500
gactgtcaag cccagttacc aagtcgttca atcgaggcga gtgctaaggc gcgccgcgcg    4560
ccagctccgt gcgaaagcct gacgcaccgg tagattcttg gtgagcccgt atcatgacgg    4620
cggcgggagc tacatggccc cgggtgattt atttttttg tatctacttc tgacccttt    4680
caaatatacg gtcaactcat cttcactgg agatgcggcc tgcttggtat tgcgatgttg    4740
tcagcttggc aaattgtggc tttcgaaaac acaaaacgat tccttagtag ccatgcattt    4800
taagataacg gaatagaaga aagaggaaat taaaaaaaa aaaaaacaa acatcccgtt    4860
cataaccgt agaatcgccg ctcttcgtgt atcccagtac cagtttattt tgaatagctc    4920
gcccgctgga gagcatcctg aatgcaagta acaaccgtag aggctgacac ggcaggtgtt    4980
gctagggagc gtcgtgttct acaaggccag acgtcttcgc ggttgatata tatgtatgtt    5040
tgactgcagg ctgctcagcg acgacagtca agttcgccct cgctgcttgt gcaataatcg    5100
cagtggggaa gccacaccgt gactcccatc tttcagtaaa gctctgttgg tgtttatcag    5160
caatacacgt aatttaaact cgttagcatg gggctgatag cttaattacc gtttaccagt    5220
gccgcggttc tgcagcttttc cttggcccgt aaaattcggc gaagccagcc aatcaccagc    5280
taggcaccag ctaaacccta taattagtct cttatcaaca ccatccgctc ccccgggatc    5340
aatgaggaga atgaggggga tgcggggcta aagaagccta cataaccctc atgccaactc    5400
ccagtttaca ctcgtcgagc caacatcctg actataagct aacacagaat gcctcaatcc    5460
tgggaagaac tggccgctga taagcgcgcc cgcctcgcaa aaaccatccc tgatgaatgg    5520
```

```
aaagtccaga cgctgcctgc ggaagacagc gttattgatt tcccaaagaa atcggggatc   5580
ctttcagagg ccgaactgaa gatcacagag gcctccgctg cagatcttgt gtccaagctg   5640
gcggccggag agttgacctc ggtggaagtt acgctagcat tctgtaaacg ggcagcaatc   5700
gcccagcagt tagtagggtc ccctctacct ctcagggaga tgtaacaacg ccaccttatg   5760
ggactatcaa gctgacgctg gcttctgtgc agacaaactg cgcccacgag ttcttccctg   5820
acgccgctct cgcgcaggca agggaactcg atgaatacta cgcaaagcac aagagacccg   5880
ttggtccact ccatggcctc cccatctctc tcaaagacca gcttcgagtc aaggtacacc   5940
gttgccccta agtcgttaga tgtccctttt tgtcagctaa catatgccac cagggctacg   6000
aaacatcaat gggctacatc tcatggctaa acaagtacga cgaaggggac tcggttctga   6060
caaccatgct ccgcaaagcc ggtgccgtct tctacgtcaa gacctctgtc ccgcagaccc   6120
tgatggtctg cgagacagtc aacaacatca tcgggcgcac cgtcaaccca cgcaacaaga   6180
actggtcgtg cggcggcagt tctggtggtg agggtgcgat cgttgggatt cgtggtggcg   6240
tcatcggtgt aggaacggat atcggtggct cgattcgagt gccggccgcg ttcaacttcc   6300
tgtacggtct aaggccgagt catgggcggc tgccgtatgc aaagatggcg aacagcatgg   6360
agggtcagga cggtgcac agcgttgtcg ggccgattac gcactctgtt gagggtgagt   6420
ccttcgcctc ttccttcttt tcctgctcta taccaggcct ccactgtcct cctttcttgc   6480
tttttatact atatacgaga ccggcagtca ctgatgaagt atgttagacc tccgcctctt   6540
caccaaatcc gtcctcggtc aggagccatg gaaatacgac tccaaggtca tccccatgcc   6600
ctggcgccag tccgagtcgg acattattgc ctccaagatc aagaacggcg gctcaatat   6660 cggctactac aacttcgacg gcaatgtcct tccacaccct cctatcctgc gcggcgtgga   6720
aaccaccgtc gccgcactcg ccaaagccgg tcacaccgtg accccgtgga cgccatacaa   6780
gcacgatttc ggccacgatc tcatctccca tatctacgcg gctgacggca gcgccgacgt   6840
aatgcgcgat atcagtgcat ccggcgagcc ggcgattcca aatatcaaag acctactgaa   6900
cccgaacatc aaagctgtta acatgaacga gctctgggac acgcatctcc agaagtggaa   6960
ttaccagatg gagtaccttg agaaatggcg ggaggctgaa gaaaaggccg ggaaggaact   7020
ggacgccatc atcgcgccga ttcgcgccta cgctgcggta cggcatgacc agttccggta   7080
ctatgggtat gcctctgtga tcaacctgct ggatttcacg agcgtggttg ttccggttac   7140
ctttgcggat aagaacatcg ataagaagaa tgagagtttc aaggcggtta gtgagcttga   7200
tgccctcgtg caggaagagt atgatccgga ggcgtaccat ggggcaccgg ttgcagtgca   7260
ggttatcgga cggagactca gtgaagagag gacgttggcg attgcagagg aagtggggaa   7320
gttgctggga aatgtggtga ctccatagct aataagtgtc agatagcaat ttgcacaaga   7380
aatcaatacc agcaactgta aataagcgct gaagtgacca tgccatgcta cgaaagagca   7440
gaaaaaaacc tgccgtagaa ccgaagagat atgacacgct tccatctctc aaaggaagaa   7500
tcccttcagg gttgcgtttc cagtctagac acgtataacg gcacaagtgt ctctcaccaa   7560
atgggttata tctcaaatgt gatctaagga tggaaagccc agaatctagg cctattaata   7620
ttccggagta tacgtagccg gctaacgtta acaaccggta cctctagaac tatagctagc   7680
atgcgcaaat ttaaagcgct gatatcgatc gcgcgcagat ccatatatag ggcccgggtt   7740
ataattacct caggtcgacg tcccatggcc attcgaattc gtaatcatgg tcatagctgt   7800
ttcctgtgtg aaattgttat ccgctcacaa ttccacacaa catacgagcc ggaagcataa   7860
agtgtaaagc ctggggtgcc taatgagtga gctaactcac attaattgcg ttgcgctcac   7920
```

```
tgcccgcttt ccagtcggga aacctgtcgt gccagctgca ttaatgaatc ggccaacgcg    7980
cggggagagg cggtttgcgt attgggcgct cttccgcttc ctcgctcact gactcgctgc    8040
gctcggtcgt tcggctgcgg cgagcggtat cagctcactc aaaggcggta atacggttat    8100
ccacagaatc aggggataac gcaggaaaga acatgtgagc aaaaggccag caaaaggcca    8160
ggaaccgtaa aaaggccgcg ttgctggcgt ttttccatag gctccgcccc cctgacgagc    8220
atcacaaaaa tcgacgctca agtcagaggt ggcgaaaccc gacaggacta taaagatacc    8280
aggcgtttcc ccctggaagc tccctcgtgc gctctcctgt tccgaccctg ccgcttaccg    8340
gatacctgtc cgcctttctc ccttcgggaa gcgtggcgct ttctcatagc tcacgctgta    8400
ggtatctcag ttcggtgtag tcgttcgct ccaagctggg ctgtgtgcac gaacccccg    8460 ttcagcccga ccgctgcgcc ttatccggta actatcgtct tgagtccaac ccggtaagac    8520
acgacttatc gccactggca gcagccactg gtaacaggat tagcagagcg aggtatgtag    8580
gcggtgctac agagttcttg aagtggtggc ctaactacgg ctacactaga agaacagtat    8640
ttggtatctg cgctctgctg aagccagtta ccttcggaaa aagagttggt agctcttgat    8700
ccggcaaaca aaccaccgct ggtagcgtg gtttttttgt ttgcaagcag cagattacgc    8760
gcagaaaaaa aggatctcaa gaagatcctt tgatcttttc tacggggtct gacgctcagt    8820
ggaacgaaaa ctcacgttaa gggattttgg tcatgagatt atcaaaaagg atcttcacct    8880
agatcctttt aaattaaaaa tgaagtttta atcaatcta agtatatat gagtaaactt    8940 ggtctgacag ttaccaatgc ttaatcagtg aggcacctat ctcagcgatc tgtctatttc    9000
gttcatccat agttgcctga ctccccgtcg tgtagataac tacgatacgg gagggcttac    9060
catctggccc cagtgctgca atgataccgc gagacccacg ctcaccggct ccagatttat    9120
cagcaataaa ccagccagcc ggaagggccg agcgcagaag tggtcctgca actttatccg    9180
cctccatcca gtctattaat tgttgccggg aagctagagt aagtagttcg ccagttaata    9240
gtttgcgcaa cgttgttgcc attgctacag gcatcgtggt gtcacgctcg tcgtttggta    9300
tggcttcatt cagctccggt tcccaacgat caaggcgagt tacatgatcc cccatgttgt    9360
gcaaaaaagc ggttagctcc ttcggtcctc cgatcgttgt cagaagtaag ttggccgcag    9420
tgttatcact catggttatg gcagcactgc ataattctct tactgtcatg ccatccgtaa    9480
gatgcttttc tgtgactggt gagtactcaa ccaagtcatt ctgagaatag tgtatgcggc    9540
gaccgagttg ctcttgcccg gcgtcaatac gggataatac cgcgccacat agcagaactt    9600
taaaagtgct catcattgga aaacgttctt cggggcgaaa actctcaagg atcttaccgc    9660
tgttgagatc cagttcgatg taacccactc gtgcacccaa ctgatcttca gcatctttta    9720
ctttcaccag cgtttctggg tgagcaaaaa caggaaggca aaatgccgca aaaagggaa    9780 taagggcgac acggaaatgt tgaatactca tactcttcct ttttcaatat tattgaagca    9840
tttatcaggg ttattgtctc atgagcggat acatatttga atgtatttag aaaaataaac    9900
aaataggggt tccgcgcaca tttccccgaa aagtgccacc tgacgtctaa gaaaccatta    9960
ttatcatgac attaacctat aaaaataggc gtatcacgag gccctttcgt ctcgcgcgtt   10020
tcggtgatga cggtgaaaac ctctgacaca tgcagctccc ggagacggtc acagcttgtc   10080
tgtaagcgga tgccgggagc agacaagccc gtcagggcgc gtcagcgggt gttggcgggt   10140
gtcggggctg gcttaactat gcggcatcag agcagattgt actgagagtg caccataaaa   10200
ttgtaaacgt taatattttg ttaaaattcg cgttaaattt ttgttaaatc agctcatttt   10260
ttaaccaata ggccgaaatc ggcaaaatcc cttataaatc aaaagaatag cccgagatag   10320
```

```
ggttgagtgt tgttccagtt tggaacaaga gtccactatt aaagaacgtg gactccaacg   10380
tcaaagggcg aaaaaccgtc tatcagggcg atggcccact acgtgaacca tcacccaaat   10440
caagtttttt ggggtcgagg tgccgtaaag cactaaatcg gaaccctaaa gggagccccc   10500
gatttagagc ttgacgggga agccggcga  acgtggcgag aaaggaaggg aagaaagcga   10560
aaggagcggg cgctagggcg ctggcaagtg tagcggtcac gctgcgcgta accaccacac   10620
ccgccgcgct taatgcgccg ctacagggcg cgtactatgg ttgctttgac gtatgcggtg   10680
tgaaataccg cacagatgcg taaggagaaa ataccgcatc aggcgccatt cgccattcag   10740
gctgcgcaac tgttgggaag ggcgatcggt gcgggcctct tcgctattac gccagctggc   10800
gaaaggggga tgtgctgcaa ggcgattaag ttgggtaacg ccagggtttt cccagtcacg   10860
acgttgtaaa acgacggcca gtgcc                                          10885

<210> SEQ ID NO 104
<211> LENGTH: 1570
<212> TYPE: DNA
<213> ORGANISM: Trichoderma reesei

<400> SEQUENCE: 104
atgtatcgga agttggccgt catctcggcc ttcttggcca cagctcgtgc tcagtcggcc     60
tgcactctcc aatcggagac tcacccgcct ctgacatggc agaaatgctc gtctggtggc    120
acttgcactc aacagacagg ctccgtggtc atcgacgcca actggcgctg gactcacgct    180
acgaacagca gcacgaactg ctacgatggc aacacttgga gctcgaccct atgtcctgac    240
aacgagacct gcgcgaagaa ctgctgtctg gacggtgccg cctacgcgtc cacgtacgga    300
gttaccacga gcggtaacag cctctccatt ggctttgtca cccagtctgc gcagaagaac    360
gttggcgctc gcctttacct tatggcgagc gacacgacct accaggaatt caccctgctt    420
ggcaacgagt tctcttttga tgttgatgtt tcgcagctgc cgtaagtgac ttaccatgaa    480
cccctgacgt atcttcttgt gggctcccag ctgactggcc aatttaaggt gcggcttgaa    540
cggagctctc tacttcgtgt ccatggacgc ggatggtggc gtgagcaagt atcccaccaa    600
caccgctggc gccaagtacg gcacggggta ctgtgacagc cagtgtcccc gcgatctgaa    660
gttcatcaat ggccaggcca acgttgaggg ctgggagccg tcatccaaca acgcaaacac    720
gggcattgga ggacacggaa gctgctgctc tgagatggat atctgggagg ccaactccat    780
ctccgaggct cttacccccc acccttgcac gactgtcggc caggagatct gcagggtga    840 tgggtgcggc ggaacttact ccgataacag atatggcggc acttgcgatc ccgatggctg    900
cgactggaac ccataccgcc tgggcaacac cagcttctac ggccctggct caagctttac    960
cctcgatacc accaagaaat tgaccgttgt cacccagttc gagacgtcgg gtgccatcaa   1020
ccgatactat gtccagaatg gcgtcacttt ccagcagccc aacgccgagc ttggtagtta   1080
ctctggcaac gagctcaacg atgattactg cacagctgag gaggcagaat tcggcggatc   1140
ctctttctca gacaagggcg gcctgactca gttcaagaag ctacctctg gcggcatggt   1200 tctggtcatg agtctgtggg atgatgtgag tttgatggac aaacatgcgc gttgacaaag   1260
agtcaagcag ctgactgaga tgttacagta ctacgccaac atgctgtggc tggactccac   1320
ctacccgaca aacgagacct cctccacacc cggtgccgtg cgcggaagct gctccaccag   1380
ctccggtgtc cctgctcagg tcgaatctca gtctcccaac gccaaggtca ccttctccaa   1440
catcaagttc ggacccattg gcagcaccgg caacccctagc ggcggcaacc ctcccggcgg   1500
aaacccgcct ggcaccacca ccacccgccg cccagccact accactggaa gctctcccgg   1560
```
acctactagt                                                            1570

<210> SEQ ID NO 105
<211> LENGTH: 480
<212> TYPE: PRT
<213> ORGANISM: Trichoderma reesei

<400> SEQUENCE: 105

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

```
Phe Lys Lys Ala Thr Ser Gly Gly Met Val Leu Val Met Ser Leu Trp
        370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
        450                 455                 460

Thr Arg Arg Pro Ala Thr Thr Thr Gly Ser Ser Pro Gly Pro Thr Ser
465                 470                 475                 480

<210> SEQ ID NO 106
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 106

Ser Pro Met Asp
1

<210> SEQ ID NO 107
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 107

Asp Leu Gly Glu
1

<210> SEQ ID NO 108
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 108

Thr Pro Thr Ala
1

<210> SEQ ID NO 109
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 109

Lys Ser Arg Ser
1

<210> SEQ ID NO 110
<211> LENGTH: 4
<212> TYPE: PRT
<213> ORGANISM: Artificial Sequence
<220> FEATURE:
<223> OTHER INFORMATION: synthetic KEX2 site presequence
```

```
<400> SEQUENCE: 110

Gly Gly Gly Ser
1

<210> SEQ ID NO 111
<211> LENGTH: 4
<212> TYPE: PRT
<213> ORGANISM: Artificial Sequence
<220> FEATURE:
<223> OTHER INFORMATION: synthetic KEX2 site presequence

<400> SEQUENCE: 111

Ser Arg Ile Ser
1
```